(12) United States Patent
Zong et al.

(10) Patent No.: US 8,515,722 B2
(45) Date of Patent: Aug. 20, 2013

(54) SYSTEM AND METHOD OF MODELING MONO-GLYCERIDES, DIGLYCERIDES AND TRIGLYCERIDES IN BIODIESEL FEEDSTOCK

(75) Inventors: Li Zong, Shanghai (CN); Sundaram Ramanathan, Lexington, MA (US); Chau-Chyun Chen, Lexington, MA (US)

(73) Assignee: Aspen Technology, Inc., Burlington, MA (US)

( * ) Notice: Subject to any disclaimer, the term of this patent is extended or adjusted under 35 U.S.C. 154(b) by 559 days.

(21) Appl. No.: 12/765,463

(22) Filed: Apr. 22, 2010

(65) Prior Publication Data

US 2010/0280810 A1    Nov. 4, 2010

Related U.S. Application Data

(60) Provisional application No. 61/174,549, filed on May 1, 2009.

(51) Int. Cl.
*G06F 7/48* (2006.01)
*G06F 7/58* (2006.01)
*G01N 31/00* (2006.01)
*G05B 21/00* (2006.01)

(52) U.S. Cl.
USPC ........ 703/11; 703/6; 703/12; 702/22; 702/25; 700/265

(58) Field of Classification Search
None
See application file for complete search history.

(56) References Cited

U.S. PATENT DOCUMENTS

2010/0137662 A1*   6/2010   Sechrist et al. ............... 585/240

OTHER PUBLICATIONS

Allen et al. "Predicting the viscosity of biodiesel fuels from their fatty acid ester composition", Fuel, vol. 78, 1319-1326 (1999).*
Yuan et al. "Predicting the temperature dependent viscosity of biodiesel fuels", Fuel, vol. 88, 1120-1126 (2009).*
Gopinath et al. "Theoretical modeling of iodine value and saponification value of biodiesel fuels from their fatty acid composition", Renewable Energy, vol. 34, 1806-1811 (2009).*
Notification Concerning Transmittal of International Preliminary Report on Patentability, International Preliminary Report on Patentability and Written Opinion for PCT/US2010/032069 dated Nov. 10, 2011.
International Search Report and Written Opinion for PCT/US2010032069 dated Dec. 14, 2010.

(Continued)

*Primary Examiner* — Jill Warden
*Assistant Examiner* — Charles D Hammond
(74) *Attorney, Agent, or Firm* — Hamilton, Brook, Smith & Reynolds, P.C.

(57) ABSTRACT

A computer-implemented method and system of modeling physical properties of biodiesel feedstock are presented. The invention method and system include (i) estimating values of a physical property of constituent fatty acid fragments of a mono-, di-, or triglyceride, and (ii) computing a value of the physical property of the mono-, di-, or triglyceride by expressing the value of the physical property of the mono-, di-, or triglyceride as a sum of the estimated values of the physical property of constituent fatty acid fragments thereof. The method and system further include repeating steps (i) and (ii) for different mono-, di-, and/or triglycerides, resulting in a plurality of computed values of the physical property of different mono-, di-, and triglycerides. The determined value of the subject physical property enables blending of the biodiesel feedstock in production of biodiesel.

9 Claims, 28 Drawing Sheets

(56) References Cited

OTHER PUBLICATIONS

Myint, L., et al., "Process analysis and optimization of biodiesel production from soybean oil", Clean Technologies and Environmental Policy, 11:263-276 , Jun. 17, 2008.

Zong, L., et al., "Fragment-based approach for estimating thermophysical properties of fats and vegetable oils for modeling biodiesel production processes", Industrial Engineering Chemistry Research, 49:876-886, Dec. 4, 2009.

Chang, A-F, et al. "Integrated process modeling and product design of biodiesel manufacturing" Ind. Eng. Chem. Res.,49.3:1197-1213, Dec. 22, 2009.

Gopinath, A., et al. "Theoretical modeling of iodine value and saponification value of biodiesel fuels from their fatty acid composition", Renewable Energy, 34.7, Jan. 4, 2009.

Huber, M.L., et al. "Model for the thermodynamic properties of a biodiesel fuel" Renewable Energy, 23.7, Jun. 12, 2009.

Abolle, A., et al. "The density and cloud point diesel oil mixtures with straight vegetable oils (SVO): Palm, cabbage palm cotton, groundnut, copra and sunflower" Biomass and Bioenergy, 33.12, Mar. 5, 2008.

Abolle, A., et al., "The viscosity of diesel oil and mixtures with straight vegetable oils: Palm, cabbage palm, cotton, groundnut, copra and sunflower" Biomass and Bioenergy, 23.9, Sep. 29, 2009.

Ceriani, R. et al., "Group Contribution Model for Predicting Viscosity of Fatty Compounds," *Journal of Chemical and Engineering Data*, 52, 965-972 (2007).

Ceriani, R., Meirelles, A. J. A., "Predicting Vapor-liquid Equilibria of Fatty Systems," *Fluid Phase Equilibria*, 215, 227-236 (2004).

Ceriani, R. et al., "Densities and Viscosities of Vegetable Oils of Nutritional Value," *Journal of Chemical and Engineering Data*, 53, 1846-1853 (2008).

Clarke, E. C. W., Glew, D. N., "Evaluation of Thermodynamic Functions from Equilibrium Constants," *Transactions of the Faraday Society*, 62, 539-547 (1966).

Domalski, E. S., "Selected Values of Heats of Combustion and Heats of Formation of Organic Compounds Containing the Elements C, H, N, O, P, and S," *Journal of Physical and Chemical Reference Data*, 1, 222-277 (1972).

Eduljee, G. H., Boyes, A. P., "Viscosity of Some Binary Liquid Mixtures of Oleic Acid and Triolein with Selected Solvents," *Journal of Chemical and Engineering Data*, 25, 249-252 (1980).

Exarchos, N. C. et al., "Viscosities and Densities of Dilute Solutions of Glycerol Trioleate + Octane, + P-xylene, + Toluene, and + Chloroform," *Journal of Chemical and Engineering Data*, 40, 567-571 (1995).

Filho A., et al., "Computer Prediction of Triacylglycerol Composition of Vegetable Oils by HRGC," *Chromatographia*, 40, 557-562 (1995).

Freedman, B., Bagby, M. O., "Heats of Combustion of Fatty Esters and Triglycerides," *Journal of the American Oil Chemists' Society*, 66, 1601-1605 (1989).

Freedman, B. et al., "Transesterification Kinetics of Soybean Oil," *Journal of the American Oil Chemists' Society*, 63, 1375-1380 (1986).

Gray, M.S., Lovegren, N.V., "Polymorphism of Saturated Triglycerides: I. 1,3-Distearo Triglycerides," *Journal of the American Oil Chemists' Society*, 55, 310-316 (1978).

Gray, M.S., Lovegren, N.V., "Polymorphism of Saturated Triglycerides: I. 1,3-Dipalmito Triglycerides," *Journal of the American Oil Chemists' Society*, 55, 601-606 (1978).

Hagemann, J. W., and Tallent, W. H., "Differential Scanning Calorimetry of Single Acid Triglycerides: Effect of Chain Length and Unsaturation," *Journal of the American Oil Chemists' Society*, 49, 118-123 (1972).

Hampson, J. W., Rothbart, H. L., "Heats of Fusion for Some Triglycerides by Differential Scanning Calorimetry," *Journal of the American Oil Chemists' Society*, 46, 143-144 (1969).

Jaeger, F. M., "Temperature Dependence of the Free Surface Energy of Liquids in Temperature Range from −80 to 1650 degrees Centigrade," *Zeitschrift füer Anorganische und Allgemeine Chemie*, 101, 1-214 (1917).

Kishore, K. et al., "Structural Effects on the Vaporization of High Molecular Weight Esters," *Journal of Physical Chemistry*, 94, 1642-1648 (1990).

Komandin, A.V., Rosolovskii, V.Y., "Densities and Molar Volumes of Some Organic Compounds over a Broad Temperature Range," *Zh. Fiz. Khim*, 33, 1280-1282 (1959).

Krisnangkura, K., "Estimation of Heat of Combustion of Triglycerides and Fatty Acid Methyl Esters," *Journal of the American Oil Chemists' Society*, 68, 56-58 (1991).

Li, P. et al., "A New Corresponding-States Group-Contribution Method (CSGC) for Estimating Vapor Pressure of Pure Compounds," *Fluid Phase Equilibria*, 101, 101-119 (1994).

Morad, N. A. et al., "Liquid Specific Heat Capacity Estimation for Fatty Acids, Triacylglycerols, and Vegetable Oils Based on Their Fatty Acid Composition," *Journal of the American Oil Chemists' Society*, 77, 1001-1005 (2000).

Morgan, J. L.R., Chazal, P.M., "The Weight of a Falling Drop and the Laws of Tate, XV. The Drop Weights of Certain Organic Liquids and the Surface Tensions and Capillary Constants Calculated from Them," *Journal of the American Chemical Society*, 35, 1821-1834 (1913).

Myint, L. L., and El-Halwagi, M. M., "Process analysis and optimization of biodiesel production from soybean oil," *Clean Techn. Environ. Policy*, DOI 10.1007/s/0098-008-0156-5 (Jun. 2008).

National Institute of Industrial Research Board, *Modern Technology of Oils, Fats and Its Derivatives*, New Delhi: National Institute of Industrial Research, p. 22 (2000).

Ndiaye, P. M. et al., "Vapor Pressure Data of Soybean Oil, Castor Oil, and Their Fatty Acid Ethyl Ester Derivatives," *Journal of Chemical and Engineering Data*, 50, 330-333 (2005).

Niir, B., *Modern Technology of Oils, Fats and Its Derivatives*. New Delhi: National Institute of Industrial Research, 9-11 (2000).

Nilsson, S.-O., Wadso, I., "Thermodynamic Properties of Some Mono-, Di-, and Tri-Esters. Enthalpies of Solution in Water at 288.15 to 318.15 K and Enthalpies of Vaporization and Heat Capacities at 298.15 K," *Journal of Chemical Thermodynamics*, 18, 673-681 (1986).

Perry, E. S. et al., "Vapor Pressure of Phlegmatic Liquids I. Simple and Mixed Triglycerides," *Journal of American Chemical Society*, 71, 3720-3726 (1949).

Phillips, J. C., Mattamal, M. M., "Correlation of Liquid Heat Capacities for Carboxylic Esters," *Journal of Chemical and Engineering Data*, 21, 228-232 (1976).

Phillips, J.C., Mattamal, G.J., "Effect of Number of Carboxyl Groups on Liquid Density of Esters of Alkylcarboxylic Acids," *Journal of Chemical and Engineering Data*, 23, 1-6 (1978).

Poling, B.E. et al., *The Properties of Gases and Liquids*, New York: McGraw-Hill Companies, 5th ed., 4.33 and 9.59-9.61 (2000).

Reid, R. C. et al., *The Properties of Gases and Liquids*, New York: McGraw-Hill, 4th ed., 439 (1987).

Rodriguez, M. et al., "Viscosity of Triglycerides + Alcohols from 278 to 313 K," *Journal of Chemical and Engineering Data*, 39, 102-105 (1994).

Ruzicka, V. Jr., Domalski, E. S., "Estimation of the Heat Capacities of Organic Liquids as a Function of Temperature Using Group Additivity. I. Hydrocarbon Compounds," *Journal of Physical and Chemical Reference Data*, 22, 597-618 (1993).

Ruzicka, V. Jr., Domalski, E. S., "Estimation of the Heat Capacities of Organic Liquids as a Function of Temperature Using Group Additivity. II. Compounds of Carbon, Hydrogen, Halogens, Nitrogen, Oxygen, and Sulfur," *Journal of Physical and Chemical Reference Data*, 22, 619-657 (1993).

Silbert, L.S. et al., "The Heats of Combustion, Formation, and Isomerization of Isomeric Monoglycerides," *The Journal of Physical Chemistry*, 69, 2887-2894 (1965).

Sum, A. K. et al., "Predictive Molecular Model for the Thermodynamics and Transport Properties of Triacylglycerols," *Journal of Physical Chemistry B*, 107, 14443-14454 (2003).

Valeri, D., Meirelles, A. J. A., "Viscosities of Fatty Acids, Triglycerides, and Their Binary Mixtures." *Journal of the American Oil Chemists' Society*, 74, 1221-1226 (1997).

Van Krevelen, D. W., *Properties of Polymers*. Amsterdam: Elsevier, 3rd ed., (1990).

Walden, P., Swinne, R., "The Capillary Constants of Liquid Esters," *Z. Phys. Chem.*, 77, 700-758 (1912).

Ward, T.L. et al., "Some Thermal Properties of 1-Monostearin, 1-Aceto 3-stearin and 1,2-Diaceto-3-stearin," *Journal of Physical Chemistry*, 59, 4-7 (1955).

Zéberg-Mikkelsen, C. K., Stenby, E. H., "Predicting the Melting Points and the Enthalpies of Fusion of Saturated Triglycerides by a Group Contribution Method," *Fluid Phase Equilibria*, 62, 7-17 (1999).

\* cited by examiner

SYSTEM AND METHOD OF MODELING MONO-GLYCERIDES, DIGLYCERIDES AND TRIGLYCERIDES IN BIODIESEL FEEDSTOCK

RELATED APPLICATION

This application claims the benefit of U.S. Provisional Application No. 61/174,549, filed on May 1, 2009.

The entire teachings of the above application are incorporated herein by reference.

BACKGROUND OF THE INVENTION

Interest has grown tremendously over the last decade in the use of fats and vegetable oils as a feedstock for manufacturing biodiesel, and many commercial plants have been built. The economic advantage of using vegetable oils as a feedstock, however, can vary significantly based on a number of factors including the fluctuating cost of crude oil, the limited supply of vegetable oils, and competing demands in food applications. Biodiesel is a renewable, alternative diesel fuel consisting of long chain alkyl (methyl or ethyl) esters, made by transesterification of vegetable oils such as those from corn, olive, palm, cottonseed and sunflower seed, or animal fats such as tallow, lard, and butter, as well as commercial products, such as margarines.

Triglycerides, also known as triacylglycerols or TAGs, are the major component of nearly all the commercially important biodiesel feedstock, such as, for example, the fats and oils of animals and plant origin listed above. Triglycerides are formed from a single molecule of glycerol, combined with three fatty acids on each of the glycerol OH groups. The chemical formula of triglycerides is $R_1COO-CH_2CH(-OOC-R_2)CH_2-OOC-R_3$, where $R_1$, $R_2$, and $R_3$ are long alkyl or alkenyl chains. The three fatty acids $R_1COOH$, $R_2COOH$ and $R_3COOH$ can be all different, all the same, or only two the same. Triglycerides with three identical fatty acids ($R_1=R_2=R_3$) are generally denoted as simple triglycerides. Triglycerides containing more than one type of fatty acid are denoted as mixed triglycerides. Chain lengths of fatty acids in natural triglycerides are variable, but carbon numbers of 16, 18 and 20 carbons are the most common. Triglycerides that include fatty acids that contain only single bonds between carbons along the chain length (alkyl chains) are denoted as saturated triglycerides. Triglycerides containing carbon-carbon double bonds between carbons along the chain length (alkenyl chains) are denoted as unsaturated triglycerides. Unsaturated triglycerides containing a single carbon-carbon double bond are denoted as monounsaturated triglycerides, while those containing two or more carbon-carbon double bonds are denoted as polyunsaturated triglycerides.

Biodiesel is produced by transesterification of triglycerides. A representative transesterification reaction that produces biodiesel in the form of methyl esters from a representative triglyceride biodiesel feedstock containing $R_1$, $R_2$, and $R_3$ fatty acids, is illustrated in FIG. 1. In the transesterification reaction, the triglyceride is reacted with alcohol, such as, for example methanol in FIG. 1, in the presence of a catalyst, typically a strong alkali such as, for example, sodium hydroxide or potassium hydroxide. The reaction can also be acid-catalyzed or enzymatic. The reaction products are glycerol and the methyl esters of the $R_1$, $R_2$, and $R_3$ fatty acids. The methyl esters can then be used as biodiesel fuel.

Most natural fats and oils are complex mixtures of many different triglycerides. The exact triglyceride composition of a fat or oil further varies with the source and growth conditions of the feedstock. Significant research has been focused on the development of new non-food vegetable oil sources as a sustainable feedstock for biodiesel manufacturing. For example, certain species of algae that contain high amounts of oil and have high growth rates are considered a promising potential feedstock for next generation biofuels. New feedstock, combined with new process technologies and optimized production plants can help to alleviate some of the cost pressures and favor the trend toward bio-chemical alternatives.

Process modeling and simulation technology has become an established practice for rapid process development and optimization in the chemical and petrochemical industry. Such technology can also play a key contributing role in the development and optimization of the process technologies and process plants for biodiesel production. One of the challenges limiting the use of process modeling and simulation technology in biodiesel processes is the lack of proven models and databanks for estimating the thermophysical properties of vegetable oils, blends, and, most importantly, the individual triglyceride components that make up the oils. Accurate estimation of the thermophysical properties, such as, for example, vapor pressure, enthalpy of vaporization, liquid heat capacity and enthalpy of formation, liquid molar volume and viscosity, is an essential first step to developing flowsheet models for design, optimization and control of biodiesel production processes. See Myint, L. L., and El-Halwagi, M. M., "Process analysis and optimization of biodiesel production from soybean oil," *Clean Techn. Environ. Policy*, DOI 10.1007/s/0098-008-0156-5 (June, 2008).

There is a limited amount of available information for estimation of thermophysical properties for triglycerides. Most of the data is based on the traditional functional group approach. For example, Ceriani and Meirelles reported a group contribution method for the estimation of the vapor pressure of fatty compounds and the optimized parameters. See Ceriani, R., Meirelles, A. J. A., "Predicting Vapor-liquid Equilibria of Fatty Systems," *Fluid Phase Equilibria*, 215, 227-236 (2004). All the fatty compounds gathered in the experimental data bank were split into eight functional groups: $CH_3$, $CH_2$, COOH, CH=cis, CH=trans, OH, COO, and $CH_2-CH-CH_2$. The same authors later extended this functional group approach to predict the viscosity of triglycerides. See Ceriani, R., Goncalves, C. B., Rabelo, J., Caruso, M., Cunha, A. C. C., Cavaleri, F. W., Batista, E. A. C., Meirelles, A. J. A., "Group Contribution Model for Predicting Viscosity of Fatty Compounds," *Journal of Chemical and Engineering Data*, 52, 965-972 (2007). Separately, a rather cumbersome group contribution method was developed to predict the melting points and the enthalpies of fusion of saturated triglycerides. See Zéberg-Mikkelsen, C. K., Stenby, E. H., "Predicting the Melting Points and the Enthalpies of Fusion of Saturated Triglycerides by a Group Contribution Method," *Fluid Phase Equilibria*, 62, 7-17 (1999). Although this approach can be used to identify a unique set of functional groups and parameters to match available experimental data for triglycerides, the functional group approach is too simplistic to model the variations in thermophysical properties of various triglycerides.

Similar difficulties are encountered in the estimation of thermophysical properties for mono- and diglycerides. Vegetable oils comprise 90-98% triglycerides and small amounts of mono- and diglycerides. Monoglycerides (monoacylglycerols or MAGs) are fatty acid monoesters of glycerol and exist in two isomeric forms, 1-monoglycerides and 2-monoglycerides, depending on the position of the ester bond on the glycerol group. Diglycerides (diacylglycerols or DAGs) consist of two fatty acid chains bonded to a glycerol molecule by ester linkages. They are typically found as 1,2-diglycerides and 1,3-diglycerides. Mono- and diglycerides are also formed as intermediates in the transesterification of triglycerides, which is believed to proceed as the three consecutive and reversible reactions shown in Eqs. 1-3:

$$TAG + ROH \leftrightarrow DAG + R'COOR \qquad (1)$$

$$DAG + ROH \leftrightarrow MAG + R'COOR \qquad (2)$$

$$MAG + ROH \leftrightarrow Glycerol + R'COOR \qquad (3)$$

see Freedman, B., Butterfield, R. O., Pryde, E. H., *Transesterification Kinetics of Soybean Oil*, Journal of the American Oil Chemists' Society, 63, 1375-1380 (1986).

Due to the importance of mono-, di- and triglycerides for the production of biodiesel, a new approach is needed for accurate and systematic correlation and estimation of the thermophysical properties of individual mono-, di-, and triglyceride components, and of the mixture properties of fats and oils in biodiesel feedstock.

SUMMARY OF THE INVENTION

The present invention addresses the foregoing problems. Generally speaking, the present invention provides a method and system of modeling physical properties of biodiesel feedstock and thus a method and system of blending biodiesel feed stock in the production of biodiesel.

In particular, presented is a computer-implemented method and system of modeling physical properties of fatty acid esters of glycerol in biodiesel feedstock that includes (i) estimating values of a physical property of constituent fatty acid fragments of a subject fatty acid ester of glycerol, and (ii) computing a value of the physical property of the subject glycerol by expressing the value of the physical property of the triglyceride as a sum of the estimated values of the physical property of constituent fatty acid fragments of the subject glycerol. The method and system further include repeating steps (i) and (ii) for different fatty acid esters of glycerol, resulting in a plurality of computed values of the physical property of different fatty acid esters of glycerol. Using the resulting plurality of computed physical property values of fatty acid esters of glycerol, the invention method and system determine a value of a subject physical property of a biodiesel feedstock by expressing the value of the subject physical property of the biodiesel feedstock as the sum of the computed physical property values (from the resulting plurality) corresponding to constituent fatty acid esters of glycerol of the biodiesel feedstock. The determined value of the subject physical property enables blending of the biodiesel feedstock in production of biodiesel.

In some embodiments, estimating values of a physical property of constituent fatty acid fragments of a fatty acid ester of glycerol further includes computing physical property parameters for a constituent fatty acid fragment by regression of known values of the physical property of fatty acid esters of glycerol. The physical property of a fatty acid ester of glycerol can include any one of vapor pressure, enthalpy of vaporization, liquid heat capacity, enthalpy of formation, liquid molar volume, viscosity, or any combination thereof. The biodiesel feedstock can include any of fats, oils, and combinations thereof. In certain embodiments, the step of repeating includes for a given fatty acid ester of glycerol repeating steps (i) and (ii) to compute values of different physical properties of the given fatty acid ester of glycerol, resulting in a plurality of computed values of different physical properties of different mono-, di-, and triglycerides. The method can further include storing the resulting plurality of computed mono-, di-, and triglyceride physical property values in a searchable data store.

In another embodiment, a biodiesel production modeling system includes a searchable data store holding physical property values of a plurality of fatty acid esters of glycerol. The searchable data store is formed by carrying out the following steps for each of different fatty acid esters of glycerol:

i) estimating values of a physical property of constituent fatty acid fragments of the subject fatty acid ester of glycerol, ii) computing the physical property of the subject glycerol by expressing a value of the physical property of the subject glycerol as a sum of the estimated values of the physical property of constituent fatty acid fragments of the subject glycerol, and iii) storing in the data store the resulting computed physical property value of the subject glycerol.

The system further includes a modeler operatively coupled to the data store such that the modeler uses the stored computed physical property values of fatty acid esters of glycerol to determine a value of the physical property of a biodiesel feedstock. In particular, the modeler expresses the value of the physical property of the biodiesel feedstock as the sum of the stored computed physical property values of fatty acid esters of glycerol corresponding to constituent triglycerides of the biodiesel feedstock.

The constituent fragment-based approach is superior to previous methods of predicting thermophysical properties of mono-, di-, and triglycerides (biodiesel feedstock generally), enabling efficient and reliable estimation of values of thermophysical properties in support of process modeling, simulation, design, and optimization of biodiesel production processes.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows. The teachings of all patents, published applications and references cited herein are incorporated by reference in their entirety.

According to the principles of the present invention, a computer-implemented method or system of modeling physical properties of triglycerides in biodiesel feedstock includes (i) estimating values of a physical property of constituent fatty acid fragments of a triglyceride, and (ii) computing a value of the physical property of the triglyceride by expressing the value of the physical property of the triglyceride as a sum of the estimated values of the physical property of constituent fatty acid fragments of the triglyceride. The method/system further includes repeating steps (i) and (ii) for different triglycerides, resulting in a plurality of computed values of the physical property of different triglycerides, and, using the resulting plurality, determining a value of a subject physical property of a biodiesel feedstock. This determination is made by expressing the value of the subject physical property of the biodiesel feedstock as a sum of values corresponding to constituent triglycerides of the biodiesel feedstock, wherein the determined value of the subject physical property enables blending of the biodiesel feedstock in production of biodiesel. The addends in the sum are from the resulting plurality of the computed triglyceride physical property values. Preferably the resulting plurality of computed triglyceride physical property values are stored in a searchable database 99 (FIG. 15) operatively coupled to a modeler (modeling engine) 91 of the present invention (detailed later).

Triglyceride structure is classified by the fatty acids present and the point of attachment of each fatty acid fragment to the glycerol fragment. Triglycerides are designated by an acronym representing the three individual fatty acids and their order on the glycerol fragment of the molecule. Table 1 lists the symbols for various fatty acid fragments discussed below.

TABLE 1

Names and Symbols for Common Fatty Acids

| Common Name | Symbol | Numerical Symbol |
|---|---|---|
| Butyric acid | Bu | C4:0 |
| Caproic acid | Co | C6:0 |
| Caprylic acid | Cy | C8:0 |
| Capric acid | C | C10:0 |
| Lauric acid | L | C12:0 |
| Myristic acid | M | C14:0 |
| Palmitic acid | P | C16:0 |
| Palmitoleic acid | Po | C16:1 |
| Stearic acid | S | C18:0 |
| Oleic acid | O | C18:1 |
| Linoleic acid | Li | C18:2 |
| Alpha-Linolenic acid | Ln | C18:3 |
| Arachidic acid | A | C20:0 |
| Behenic acid | B | C22:0 |
| Erucic acid | E | C22:1 |

Figure 3:
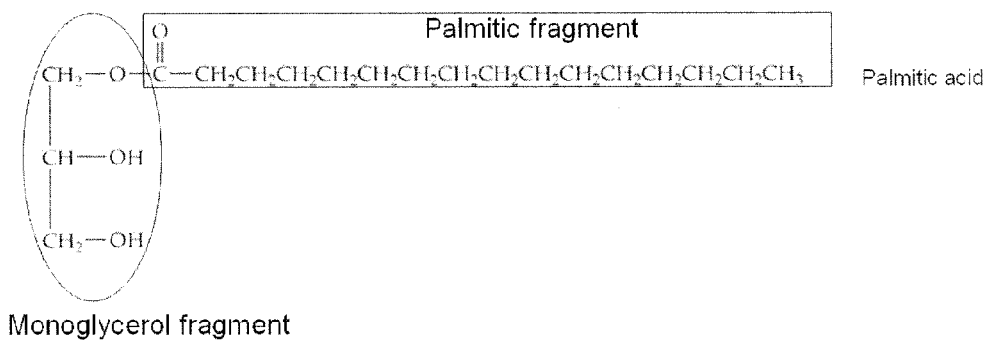
FIG. 3 is a representation of a monoglyceride component made up of a backbone monoglycerol fragment with one fatty acid fragment attached.
Figure 4:
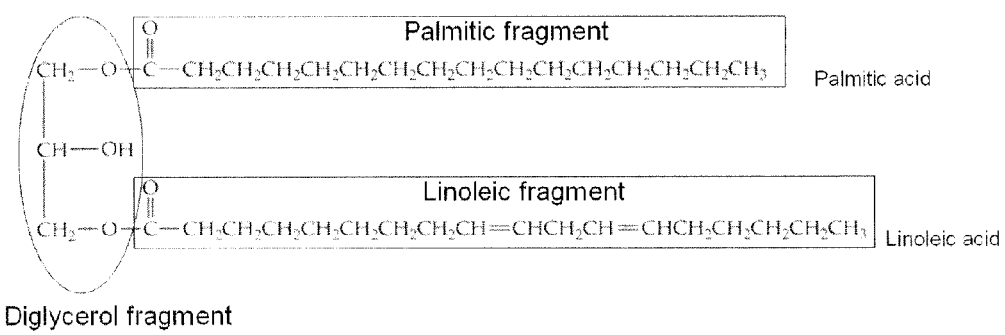
FIG. 4 is a representation of a diglyceride component made up of a backbone diglycerol fragment with two fatty acid fragments attached.

As illustrative examples, trimyristin is composed of three myristic acid fragments, and tripalmitin is composed of three palmitic acid fragments. Therefore, trimyristin can be denoted by MMM and tripalmitin by PPP. A mixed triglyceride made from two palmitic acid fragments in the outer position and one myristic acid fragment in the middle position of the glycerol fragment can be denominated as PMP. Triglyceride molecules are also denoted by a convenient shorthand designation, also listed in Table 1, showing the number of carbon atoms and the number of double bonds of the constituent fatty acids. Palmitic acid, for example, has no carbon-carbon double bonds along its 16 carbon chain, and therefore can be denoted as (C16:0), while palmitoleic acid, which has one double bond, can be denoted as (C16:1), as shown in Table 1. Following the same approach, as shown in FIG. 3, a monoglyceride component is considered as a compound made up of a backbone monoglycerol fragment with one fatty acid fragment attached. As shown in FIG. 4, a diglyceride component is considered as a compound made up of a backbone diglycerol fragment with two fatty acid fragments attached.

A biodiesel feedstock, such as, for example, crude cottonseed oil, is composed of a mixture of triglyceride components, listed in Table 2 (using the symbols listed in Table 1), based on the estimates of Ceriani and Meirelles, following the composition measurement procedure of Filho et al. See Filho A., N. R., Mendes, O. L., Lancas, F. M., "Computer Prediction of Triacylglycerol Composition of Vegetable Oils by HRGC," *Chromatographia*, 40, 557-562 (1995).

TABLE 2

Triglyceride Components for Crude Cottonseed Oil

| Triglyceride | Weight % |
|---|---|
| LOP | 0.09 |
| PPoP | 0.62 |
| POP | 3.67 |
| POS | 0.54 |
| POA | 0.07 |
| LLiP | 0.26 |
| MLiP | 1.16 |
| PLiP | 13.74 |
| PLiS | 3.91 |

TABLE 2-continued

Triglyceride Components for Crude Cottonseed Oil

| Triglyceride | Weight % |
|---|---|
| PLiA | 0.39 |
| LOLi | 0.19 |
| PPoLi | 1.93 |
| POLi | 14.3 |
| SOLi | 1.31 |
| OLiA | 0.09 |
| LLiLi | 0.23 |
| MLiLi | 1.11 |
| PLiLi | 26.58 |
| SLiLi | 4.75 |
| LiLiA | 0.17 |
| PoLiLi | 1.3 |
| OLiLi | 10.43 |
| LiLiLi | 12.88 |
| LiLiLn | 0.28 |
| Sum | 100 |

Figure 1:
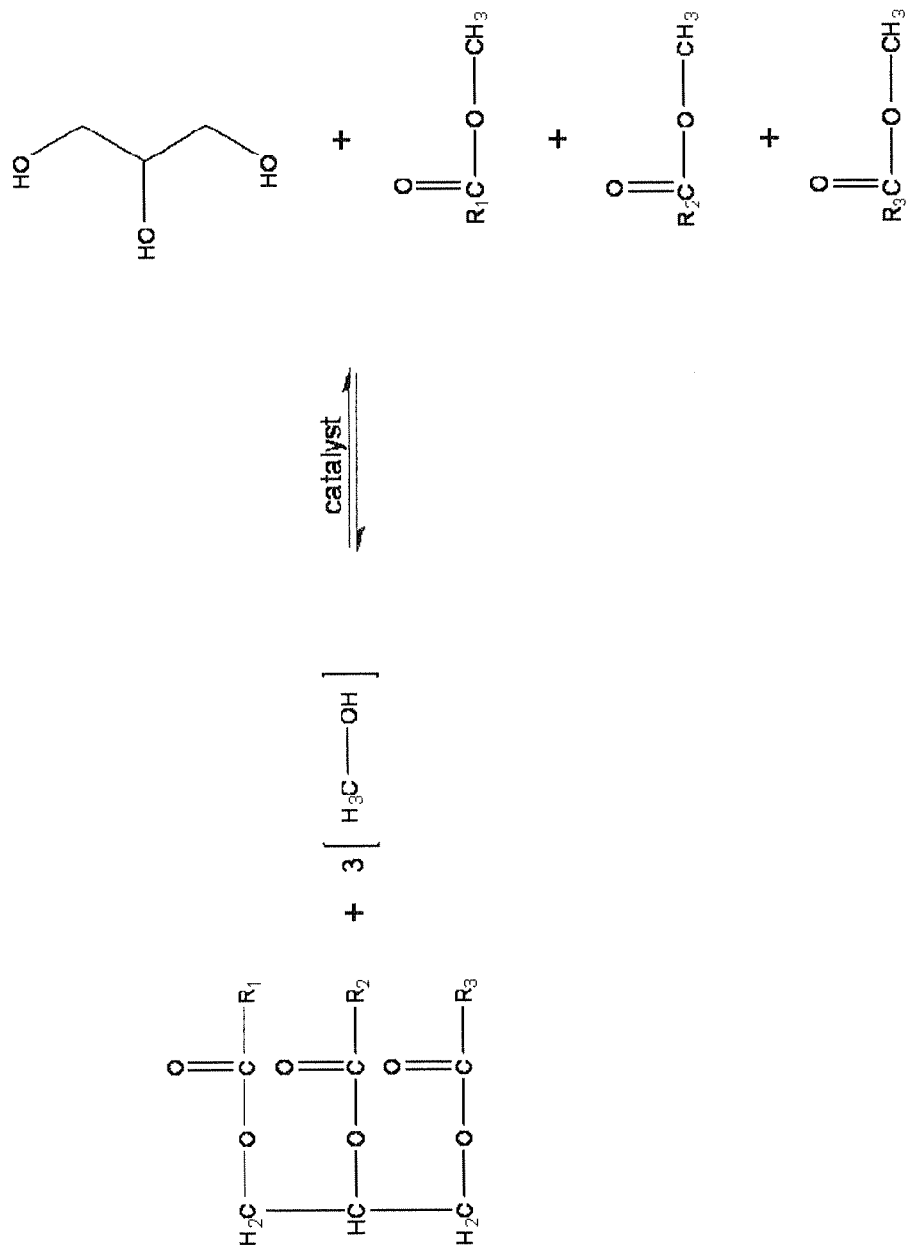
FIG. 1 is a representative transesterification reaction used for the production of biodiesel.
Figure 2:
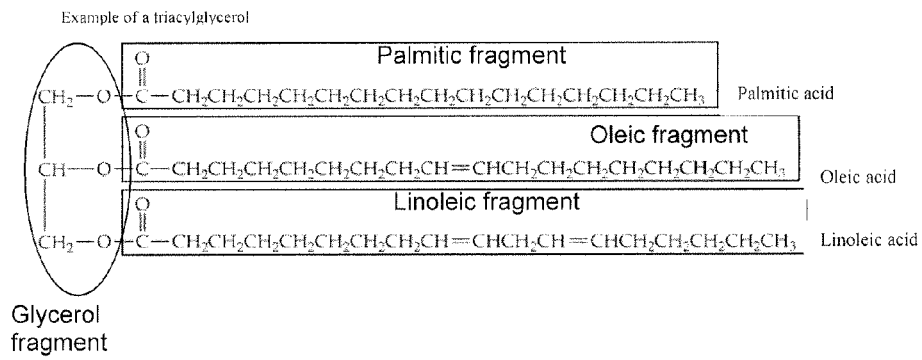
FIG. 2 is a representation of fragments of a triglyceride.

In the constituent fragment-based approach, the triglyceride components in biodiesel feedstock, such as, for example, the crude cottonseed oil listed in Table 2, are treated as compounds made up of a backbone glycerol fragment with three fatty acid fragments attached, and the thermophysical properties of a triglyceride component are calculated from the composition of the constituent fragments that make up the triglyceride component and a set of fragment-specific parameters. FIG. 2 illustrates a structural characterization of a glycerol fragment and three fatty acid fragments for an example triglyceride compound. The fragment approach enables accurate predictions of pure component properties of mixed triglycerides from the available experimental data for simple triglycerides. One structural effect not considered in the constituent fragment-based approach is the stereo-specific effect, because the fragment-based approach assumes that the contribution of each fatty acid fragment to the properties of triglyceride compounds is independent of position of the fatty acid fragment on the glycerol backbone fragment. The fragment-specific parameters for calculating thermophysical properties of triglycerides are obtained by regression of the limited experimental data available in the literature. The same approach can be applied to calculating thermophysical properties of mono- and diglycerides. Following the fragment approach, a monoglyceride component is considered as a compound made up of a backbone monoglycerol fragment with one fatty acid fragment attached. A diglyceride component is regarded as a compound made up of a backbone diglycerol fragment with two fatty acid fragments attached. Thermophysical properties of mono- or diglyceride components are then calculated from the composition of the constituent fragments and a set of fragment-specific parameters. As discussed above, the current fragment approach ignores the position isomerism effect because it assumes the contribution of each fatty acid fragment to the properties of mono- and diglyceride components is independent of position of the fatty acid fragment on the glycerol backbone fragment. This assumption is made due to the lack of experimental data available for the position isomerism effect. Therefore, from the perspective of thermophysical property calculations, 1-monoglyceride is regarded as the same as 2-monoglyceride while 1,2-diglyceride is regarded as the same as 1,3-diglyceride.

Vapor Pressure and Enthalpy and Gibbs Free Energy of Vaporization

The vapor pressure of a triglyceride component is estimated from Eq. (4):

$$\log P_i(T) = A - \frac{B}{T} = \frac{-\Delta G_\theta^{vap}}{R\theta \ln 10} + \frac{\Delta H_\theta^{vap}}{R \ln 10}\left(\frac{1}{\theta} - \frac{1}{T}\right) \quad (4)$$

where
A and B: Vapor pressure temperature dependency parameters
$P_i$: Vapor pressure of triglyceride component i, (Pa)
T: Temperature, (K)
R: Gas constant
θ: Reference temperature, 298.15 K
$\Delta H_\theta^{vap}$: Enthalpy of vaporization at reference temperature θ
$\Delta G_\theta^{vap}$: Gibbs free energy of vaporization at reference temperature θ.

Eq. 4 relates vapor pressure and temperature with enthalpy $\Delta H_\theta^{vap}$ and Gibbs free energy $\Delta G_\theta^{vap}$ of vaporization. See Clarke, E. C. W., Glew, D. N., "Evaluation of Thermodynamic Functions from Equilibrium Constants," *Transactions of the Faraday Society*, 62, 539-547 (1966). Perry reported vapor pressure temperature dependency parameters for some common simple and mixed triglycerides. See Perry, E. S., Weber, W. H., Daubert, B. F., "Vapor Pressure of Phlegmatic Liquids I. Simple and Mixed Triglycerides," *Journal of American Chemical Society*, 71, 3720-3726 (1949). The relationships cover the temperature range from 323.15 K to 573.15 K. $\Delta H_\theta^{vap}$ and $\Delta G_\theta^{vap}$ values of triglycerides listed in Table 3 were calculated from the parameters reported by Perry for the triglycerides.

TABLE 3

Calculated Physical Constants from Vapor Pressures of Triglycerides

| Material | Carbons | A | B | $\Delta H_\theta^{vap}$ (J/kmol) | $\Delta G_\theta^{vap}$ (J/kmol) |
|---|---|---|---|---|---|
| Tributyrin | 4:4:4 | 12.495 | 4250 | 8.137E+07 | 1.004E+07 |
| Tricaproin | 6:6:6 | 12.945 | 4950 | 9.477E+07 | 2.088E+07 |
| Tricaprylin | 8:8:8 | 14.245 | 6060 | 1.160E+08 | 3.471E+07 |
| Tricaprin | 10:10:10 | 14.205 | 6510 | 1.246E+08 | 4.355E+07 |
| Trilaurin | 12:12:12 | 14.705 | 7190 | 1.377E+08 | 5.371E+07 |
| Trimyristin | 14:14:14 | 14.905 | 7720 | 1.478E+08 | 6.272E+07 |
| Tripalmitin | 16:16:16 | 15.525 | 8400 | 1.608E+08 | 7.220E+07 |
| Tristearin | 18:18:18 | 15.725 | 8750 | 1.675E+08 | 7.776E+07 |
| 1-capryl-2-lauryl-3-myristin | 10:12:14 | 14.025 | 6880 | 1.317E+08 | 5.166E+07 |
| 1-lauryl-2-myristyl-3-palmitin | 12:14:16 | 14.925 | 7720 | 1.478E+08 | 6.261E+07 |
| 1-myristyl-2-palmityl-3-stearin | 14:16:18 | 15.305 | 8250 | 1.579E+08 | 7.058E+07 |
| 1-myristyl-2-capryl-3-stearin | 14:10:18 | 15.005 | 7750 | 1.484E+08 | 6.272E+07 |
| 1-myristyl-2-lauryl-3-stearin | 14:12:18 | 14.965 | 7860 | 1.505E+08 | 6.506E+07 |
| 1-palmityl-2-capryl-3-stearin | 16:10:18 | 15.425 | 8090 | 1.549E+08 | 6.684E+07 |
| 1-palmityl-2-lauryl-3-stearin | 16:12:18 | 15.675 | 8360 | 1.601E+08 | 7.058E+07 |

Figure 5A:
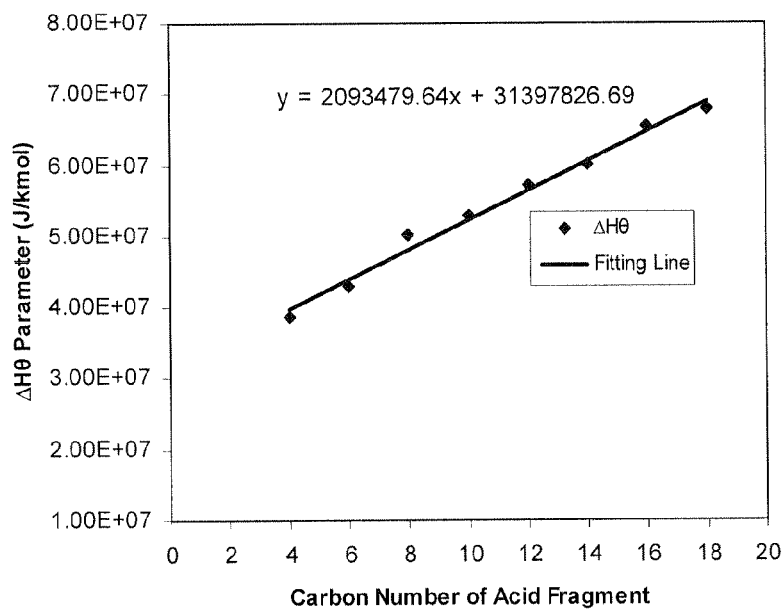
FIG. 5A is a graph of the relationship between $\Delta H_{\theta,A}^{vap}$ for fragments and carbon number of each saturated acid fragment.
Figure 5B:
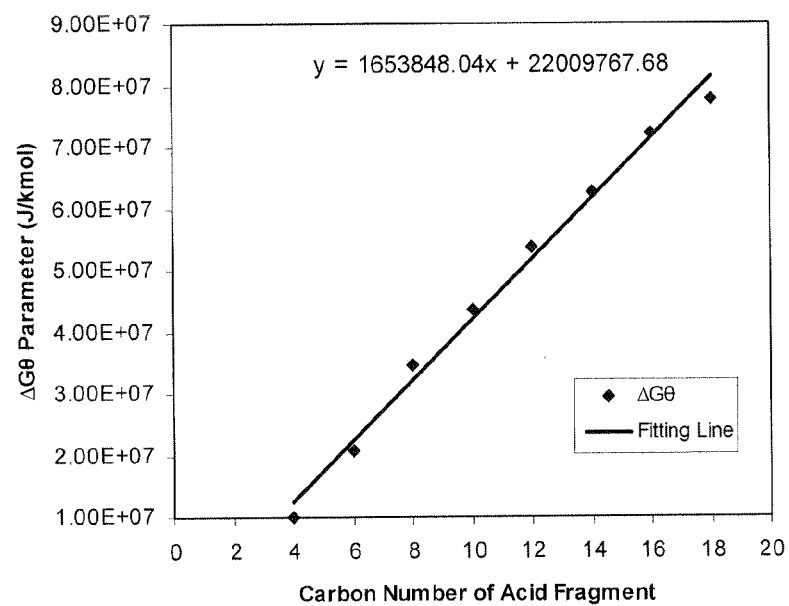
FIG. 5B is a graph of the relationship between $\Delta G_{\theta,A}^{vap}$ for fragments and carbon number of each saturated acid fragment.

Values of fragment-specific enthalpy and Gibbs free energy of vaporization from fragment compositions of triglycerides were calculated from Eqs. (5) and (6):

$$\Delta H_\theta^{vap} = N_{frag} \sum_A^{N_{frag}} x_A \Delta H_{\theta,A}^{vap} \quad (5)$$

$$\Delta G_\theta^{vap} = N_{frag} \sum_A^{N_{frag}} x_A \Delta G_{\theta,A}^{vap} \quad (6)$$

where
$N_{frag}$: Number of fragments in the triglyceride
$x_A$: Mole fraction of fragment A in the triglyceride $\Delta H_{\theta,A}^{vap}$: Enthalpy of vaporization contribution of fragment A
$\Delta G_{\theta,A}^{vap}$: Gibbs free energy of vaporization contribution of fragment A FIGS. 5A and 5B show the relationships between $\Delta H_{\theta,A}^{vap}$ and $\Delta G_{\theta,A}^{vap}$ parameters, respectively, for the fragments and the carbon number of each fatty acid fragment. The trend line equations are displayed on the charts in respective FIGS. 5A and 5B. The parameters for the saturated fragments with long chains, such as C20 and C22, can be extrapolated from the trend line equations. The calculated parameters $\Delta H_{\theta,A}^{vap}$ and $\Delta G_{\theta,A}^{vap}$ for the glycerol fragment and fatty acid fragments with carbon numbers ranging from 4 to 22 are listed in Table 4.

TABLE 4

Calculated Vapor Pressure Fragment Parameters $\Delta H_{\theta,A}^{vap}$ and $\Delta G_{\theta,A}^{vap}$

| Fragments | Symbols | Carbons | $\Delta H_{\theta,A}^{vap}$ [J/kmol] | $\Delta G_{\theta,A}^{vap}$ [J/kmol] |
|---|---|---|---|---|
| Monoglycerol | | | 4.173E+07 | −1.986E+07 |
| Diglycerol | | | 3.486E+06 | −4.687E+07 |
| triglycerol | Gly-frag | | −3.476E+07 | −7.388E+07 |
| Butyric | Bu-frag | C4:0 | 3.862E+07 | 2.789E+07 |
| Caproic | Co-frag | C6:0 | 4.307E+07 | 3.148E+07 |
| Caprylic | Cy-frag | C8:0 | 5.015E+07 | 3.609E+07 |
| Capric | C-frag | C10:0 | 5.292E+07 | 3.904E+07 |
| Lauric | L-frag | C12:0 | 5.707E+07 | 4.233E+07 |
| Myristic | M-frag | C14:0 | 6.006E+07 | 4.515E+07 |
| Palmitic | P-frag | C16:0 | 6.550E+07 | 4.877E+07 |
| Palmitoleic | Po-frag | C16:1 | 6.550E+07 | 4.877E+07 |

TABLE 4-continued

Calculated Vapor Pressure Fragment Parameters $\Delta H_{\theta,A}^{vap}$ and $\Delta G_{\theta,A}^{vap}$

| Fragments | Symbols | Carbons | $\Delta H_{\theta,A}^{vap}$ [J/kmol] | $\Delta G_{\theta,A}^{vap}$ [J/kmol] |
|---|---|---|---|---|
| Stearic | S-frag | C18:0 | 6.800E+07 | 5.088E+07 |
| Oleic | O-frag | C18:1 | 6.800E+07 | 5.088E+07 |
| Linoleic | Li-frag | C18:2 | 6.800E+07 | 5.088E+07 |
| Linolenic | Ln-frag | C18:3 | 6.800E+07 | 5.088E+07 |
| Arachidic | A-frag | C20:0 | 7.327E+07 | 5.509E+07 |
| Behenic | B-frag | C22:0 | 7.745E+07 | 5.839E+07 |
| Erucic | E-frag | C22:1 | 7.745E+07 | 5.839E+07 |

The calculated parameters $\Delta H_{\theta,A}^{vap}$ and $\Delta G_{\theta,A}^{vap}$ for the glycerol fragment were calculated from the known values of the enthalpy and Gibbs free energy of vaporization of triglycerides listed in Table 3, by using the fact that the glycerol fragment is one and the same in all of the triglycerides, to calculate the optimal value of the enthalpy and Gibbs free energy of the glycerol fragment that best matches the respective values for the triglycerides listed in Table 3.

To the applicants' knowledge, experimental data for vapor pressures of unsaturated triglycerides such as trilinolein (C18:2) and trilinolenin (C18:3) are not available to identify the fragment-specific parameters. Until such data become available, the effect of double bonds on the vapor pressure of triglyceride molecules is assumed to be negligible. In other words, the vapor pressure of unsaturated triglycerides is regarded as the same as that of the saturated triglyceride with the same carbon number (number of carbon atoms in the fatty acid chain). Likewise, the effect of double bonds per triglyceride molecule on the enthalpy of vaporization is also assumed to be negligible.

Eqs. (5) and (6) can be used to estimate the enthalpy of vaporization and Gibbs free energy of vaporization for any triglycerides that are composed of the fragments reported in Table 4. For example, the enthalpy of vaporization of tributyrin can be obtained from Eq (5) as:

$$3*(3.862E+07*(1/3)+3.862E+07*(1/3)+3.862E+07*(1/3))-3.476E+07=8.11E+07 \quad (7)$$

The value calculated in Eq. (7) of the enthalpy of vaporization of tributyrin is in good agreement with the literature value (8.137E+07) listed in Table 3.

Given the enthalpy of vaporization and Gibbs free energy of vaporization for the triglyceride, Eq. (4) can be used to compute the temperature-dependent vapor pressure for the triglyceride component of a biodiesel feedstock. The vapor pressure of the biodiesel feedstock that contains a plurality of triglyceride components can be obtained from Dalton's law:

$$P = \sum_{i=1}^{N} x_i P_i \quad (8)$$

where
P: Vapor pressure of biodiesel feedstock, (Pa)
N: Number of triglyceride components in the biodiesel feedstock
$P_i$: Vapor pressure of triglyceride component i, (Pa)
$x_i$: Mole fraction of triglyceride component i in the biodiesel feedstock.

$\Delta H_{\theta,A}^{vap}$ and $\Delta G_{\theta,A}^{vap}$ values for the monoglycerol fragment listed in Table 4 were regressed against the limited vapor pressure data of monoglycerides. See National Institute of Industrial Research Board, *Modern Technology of Oils, Fats and Its Derivatives*, New Delhi: National Institute of Industrial Research, p. 22 (2000).

To the Applicants' knowledge, experimental data for vapor pressures of diglycerides are not available for the identification of the diglycerol fragment-specific parameters. Until such data become available, Applicants in one embodiment choose to average the $\Delta H_{\theta,A}^{vap}$ and $\Delta G_{\theta,A}^{vap}$ parameters of mono- and triglycerol fragments to obtain the respective parameters for the diglycerol fragment. Table 4 tabulates calculated $\Delta H_{\theta,A}^{vap}$ and $\Delta G_{\theta,A}^{vap}$ parameters for the three glycerol fragments and the fatty acid fragments with carbon numbers ranging from 4 to 22. Eqs. 5 and 6 are then used to estimate enthalpy of vaporization and Gibbs free energy of vaporization for any mono-, di-, and triglycerides made up of the fragments reported in Table 4. Eq. 4 is then used to compute vapor pressure for the mono-, di-, and triglyceride components at any temperature.

Heat Capacity

The heat capacities of triglyceride components are calculated from the fragment composition and the fragment heat capacity parameters:

$$C_p^l = N_{frag} \sum_{A}^{N_{frag}} x_A C_{p,A}^l(T) \quad (9)$$

where
$C_{p,A}^l$: Liquid heat capacity of fragment A in the triglyceride component, (J/kmol-K)
$N_{frag}$: Number of fragments in the triglyceride component
$x_A$: Mole fraction of fragment A in the triglyceride component.

The heat capacity of fragment A, $C_{p,A}^l$, is calculated using the following linear relationship for temperature dependency:

$$C_{p,A}^l = A_{1,A} + A_{2,A} T \quad (10)$$

where
$A_{1,A}$ and $A_{2,A}$: Temperature dependency correlation parameters
T: Temperature, (K).

Figure 6A:
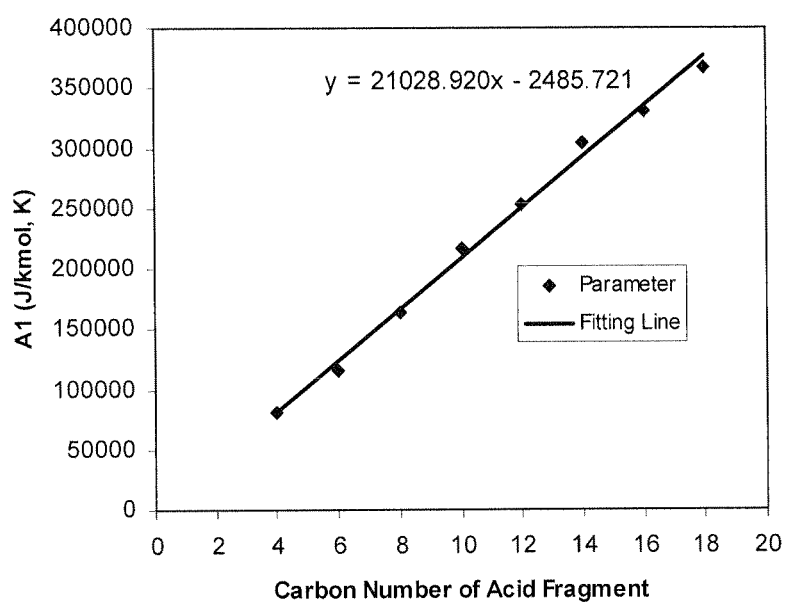
FIG. 6A is a graph of the relationship between fragment parameter $A_{1,A}$ and carbon number of each saturated acid fragment.
Figure 6B:
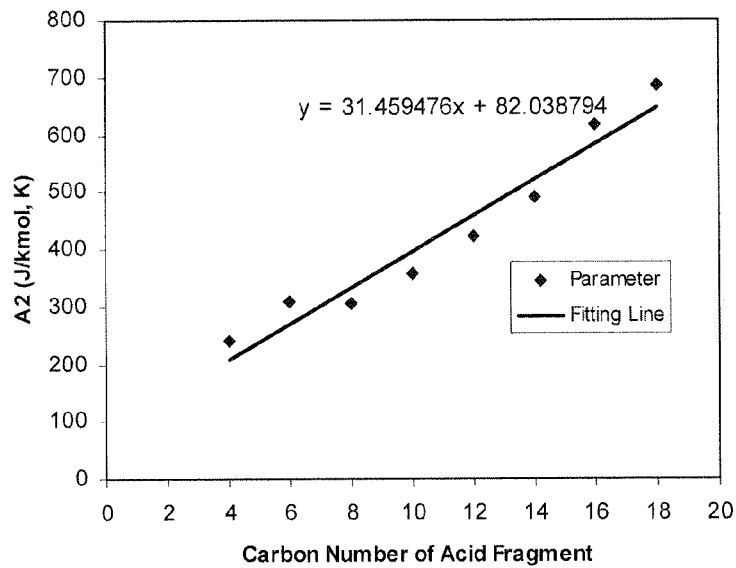
FIG. 6B is a graph of the relationship between fragment parameter $A_{2,A}$ and carbon number of each saturated acid fragment.

The parameters $A_{1,A}$ and $A_{2,A}$ for the glycerol fragment and saturated fatty acid fragments with carbon number ranging from 4 to 18 were obtained by regression against literature heat capacity data ranging from 298.15 K to 453.15 K. See Morad, N. A., Kamal, A. A. M., Panau, F., Yew, T. W., "Liquid Specific Heat Capacity Estimation for Fatty Acids, Triacylglycerols, and Vegetable Oils Based on Their Fatty Acid Composition," *Journal of the American Oil Chemists' Society*, 77, 1001-1005 (2000); Phillips, J. C., Mattamal, M. M., "Correlation of Liquid Heat Capacities for Carboxylic Esters," *Journal of Chemical and Engineering Data*, 21, 228-232 (1976). FIGS. 6A and 6B show the relationship between $A_{1,A}$ and $A_{2,A}$, respectively, and carbon number of each fatty acid fragment respectively. The trend line equations are displayed on the chart in respective FIGS. 6A and 6B. The parameters for the saturated fragments with long chains, such as C20 and C22, can be extrapolated from the linear equations.

Accounting for unsaturated fatty acid fragments is slightly different from the calculation of vapor pressure because heat capacity data is available for the unsaturated triglyceride triolein (C18:1). Applicants treat heat capacities of the polyunsaturated triglycerides trilinolein (C18:2) and trilinolenin (C18:3) as being equal to that of monounsaturated triolein (C18:1). Table 5 summarizes the calculated parameters $A_{1,A}$ and $A_{2,A}$ for the glycerol fragment and fatty acid fragments with carbon numbers ranging from 4 to 22.

TABLE 5

Calculated Liquid Heat Capacity Fragment Parameters $A_{1,A}$ and $A_{2,A}$

| Fragments | Symbols | Carbons | $A_{1,A}$ (J/kmol, K) | $A_{2,A}$ (J/kmol, K) |
|---|---|---|---|---|
| monoglycerol | | | 3.6876E+05 | 148.23 |
| diglycerol | | | 2.1506E+05 | 148.23 |
| triglycerol | Gly-frag | | 6.1355E+04 | 148.23 |
| Butyric | Bu-frag | C4:0 | 8.0920E+04 | 239.39 |
| Caproic | Co-frag | C6:0 | 1.1557E+05 | 308.41 |
| Caprylic | Cy-frag | C8:0 | 1.6402E+05 | 304.95 |
| Capric | C-frag | C10:0 | 2.1575E+05 | 357.35 |
| Lauric | L-frag | C12:0 | 2.5335E+05 | 422.23 |

TABLE 5-continued

Calculated Liquid Heat Capacity Fragment Parameters $A_{1,A}$ and $A_{2,A}$

| Fragments | Symbols | Carbons | $A_{1,A}$ (J/kmol, K) | $A_{2,A}$ (J/kmol, K) |
|---|---|---|---|---|
| Myristic | M-frag | C14:0 | 3.0377E+05 | 490.30 |
| Palmitic | P-frag | C16:0 | 3.3036E+05 | 616.35 |
| Palmitoleic | Po-frag | C16:1 | 3.3036E+05 | 616.35 |
| Stearic | S-frag | C18:0 | 3.6693E+05 | 685.76 |
| Oleic | O-frag | C18:1 | 3.9760E+05 | 540.89 |
| Linoleic | Li-frag | C18:2 | 3.9760E+05 | 540.89 |
| Linolenic | Ln-frag | C18:3 | 3.9760E+05 | 540.89 |
| Arachidic | A-frag | C20:0 | 4.1809E+05 | 711.23 |
| Behenic | B-frag | C22:0 | 4.6015E+05 | 774.15 |
| Erucic | E-frag | C22:1 | 4.6015E+05 | 774.15 |

For the mono- and diglycerol fragments, Applicants assume that the dependence on temperature of the heat capacity contribution for mono-, di- and triglycerol fragments is the same. That means that the $A_{2,A}$ parameters for the mono- and diglycerol fragments are equal to the existing $A_{2,A}$ parameter for the triglycerol fragment, as listed in Table 5. Available liquid heat capacity data for 1-monostearin [C18:0] show a large variation in heat capacity over a small temperature range. Ward, T. L., Vicknair, E. J., Singleton, W. S., Feuge, R. O., *Some Thermal Properties of* 1-*Monostearin,* 1-*Aceto* 3-*stearin and* 1,2-*Diaceto*-3-*stearin*, Journal of Physical Chemistry, 59, 4-7 (1955). In one embodiment, Applicants choose to use the average heat capacity value at the average temperature instead of the actual experimental data of 1-monostearin. The parameter $A_{1,A}$ for the monoglycerol fragment is then calculated from the average heat capacity value of 1-monostearin based on Eqs. 4 and 5.

Due to lack of reliable experimental data for diglycerides, the parameter $A_{1,A}$ of the diglycerol fragment is calculated by averaging those of the monoglycerol fragment and the triglycerol fragment. Table 5 summarizes the calculated parameters $A_{1,A}$ and $A_{2,A}$ for the three glycerol fragments and the fatty acid fragments with carbon numbers ranging from 4 to 22.

Heat of Fusion

The heat of fusion for mono-, di- and triglycerides are calculated from the fragment composition and the heat of fusion contributions for the fragments:

$$\Delta H^{fus} = \sum_A N_{frag,A} \Delta H_A^{fus} \quad (11)$$

where
$\Delta H_A^{fus}$: Heat of fusion contribution of fragment A, kJ/mol
$N_{frag,A}$: Number of fragments A in the component.
Heats of fusion contributions for the triglycerol fragment and the fatty acid fragments with carbon numbers ranging from 2 to 22 are regressed against available experimental data on heats of fusion for 25 simple and mixed triglycerides. See Gray, M. S., Lovegren, N. V., *Polymorphism of Saturated Triglycerides: I.* 1,3-*Distearo Triglycerides*, Journal of the American Oil Chemists' Society, 55, 310-316 (1978); Gray, M. S., Lovegren, N. V., *Polymorphism of Saturated Triglycerides: I.* 1,3-*Dipalmito Triglycerides*, Journal of the American Oil Chemists' Society, 55, 601-606 (1978); Hampson, J. W., Rothbart, H. L., *Heats of Fusion for Some Triglycerides by Differential Scanning Calorimetry*, Journal of the American Oil Chemists' Society, 46, 143-144 (1969); Hagemann, J. W., Tallent, W. H., *Differential Scanning Calorimetry of Single Acid Triglycerides: Effect of Chain Length and Unsaturation*, Journal of the American Oil Chemists' Society, 49, 118-123 (1972); Zéberg-Mikkelsen, C. K., Stenby, E. H., *Predicting the Melting Points and the Enthalpies of Fusion of Saturated Triglycerides by a Group Contribution Method*, Fluid Phase Equilibria, 162, 7-17 (1999). The heat of fusion contributions for the triglycerol fragment and the fatty acid fragments are listed in Table 6.

TABLE 6

Calculated Heat of Fusion Fragment Parameters $\Delta H_A^{fus}$

| Fragments | Symbols | Carbons | $\Delta H_A^{fus}$ (kJ/mol) |
|---|---|---|---|
| Monoglycerol | Monogly-frag | | 21.569 |
| Diglycerol | Digly-frag | | 21.569 |
| Triglycerol | Trigly-frag | | 21.569 |
| Acetic acid | Ac-frag | C2:0 | 1.3919 |
| Butyric acid | Bu-frag | C4:0 | 0.9904 |
| Caproic acid | Co-frag | C6:0 | 8.2682 |
| Caprylic acid | Cy-frag | C8:0 | 13.668 |
| Capric acid | C-frag | C10:0 | 24.598 |
| Lauric acid | L-frag | C12:0 | 32.868 |
| Myristic acid | M-frag | C14:0 | 37.199 |
| Palmitic acid | P-frag | C16:0 | 43.789 |
| Palmitoleic acid | Po-frag | C16:1 | 23.766 |
| Stearic acid | S-frag | C18:0 | 46.326 |
| Oleic acid | O-frag | C18:1 | 24.671 |
| Linoleic acid | Li-frag | C18:2 | 21.000 |
| Linolenic acid | Ln-frag | C18:3 | 21.000 |
| Arachidic acid | A-frag | C20:0 | 67.105 |
| Behenic acid | B-frag | C22:0 | 80.166 |
| Erucic acid | E-frag | C22:1 | 41.309 |

The heat of fusion fragment parameters are only valid for the phase transition between liquid triglycerides and their most thermodynamically stable polymorphs. The differences among heat of fusion contributions of the mono-, di- and triglycerol fragments are ignored because experimental data on heats of fusion for mono- and diglycerides are not available. In other words, in one embodiment the $\Delta H_A^{fus}$ values of the mono- and diglycerol fragments are regarded as the same as that of the triglycerol fragment, as listed in Table 6. Eq. 11 is then used to estimate heat of fusion for mono- and diglycerides made up of the fatty acid fragments reported in Table 6.

For example, as monoglycerides are composed of one monoglycerol fragment and one fatty acid fragment, Eq. 11 is applied for monoglyceride components as $$\Delta H_{monoglyceride}^{fus} = \Delta H_{monoglycerol\,frag}^{fus} + \Delta H_{fatty\,acid\,frag}^{fus} \quad (12)$$

where
$\Delta H_{monoglycerol\,frag}^{fus}$: heat of fusion contribution of the monoglycerol fragment, kJ/mol
$\Delta H_{fatty\,acid\,frag}^{fus}$: heat of fusion contribution of the fatty acid fragment, kJ/mol.

Enthalpy of Formation

Enthalpies of formation for various simple triglycerides were derived from literature data for enthalpy of combustion and enthalpy of fusion. For enthalpy of combustion data see Domalski, E. S., "Selected Values of Heats of Combustion and Heats of Formation of Organic Compounds Containing the Elements C, H, N, O, P, and S," *Journal of Physical and Chemical Reference Data*, 1, 222-277 (1972); Freedman, B., Bagby, M. O., "Heats of Combustion of Fatty Esters and Triglycerides," *Journal of the American Oil Chemists' Society*, 66, 1601-1605 (1989); Krisnangkura, K., "Estimation of Heat of Combustion of Triglycerides and Fatty Acid Methyl Esters," *Journal of the American Oil Chemists' Society*, 68, 56-58 (1991); for enthalpy of combustion data see Zéberg-Mikkelsen, C. K., Stenby, E. H., "Predicting the Melting Points and the Enthalpies of Fusion of Saturated Triglycerides by a Group Contribution Method," *Fluid Phase Equilibria*, 162, 7-17 (1999); Hampson, J. W., Rothbart, H. L., "Heats of Fusion for Some Triglycerides by Differential Scanning Calorimetry," *Journal of the American Oil Chem-*

*ists' Society*, 46, 143-144 (1969); Hagemann, J. W., and Tallent, W. H., "Differential Scanning Calorimetry of Single Acid Triglycerides: Effect of Chain Length and Unsaturation," *Journal of the American Oil Chemists' Society*, 49, 118-123 (1972).

Figure 7:
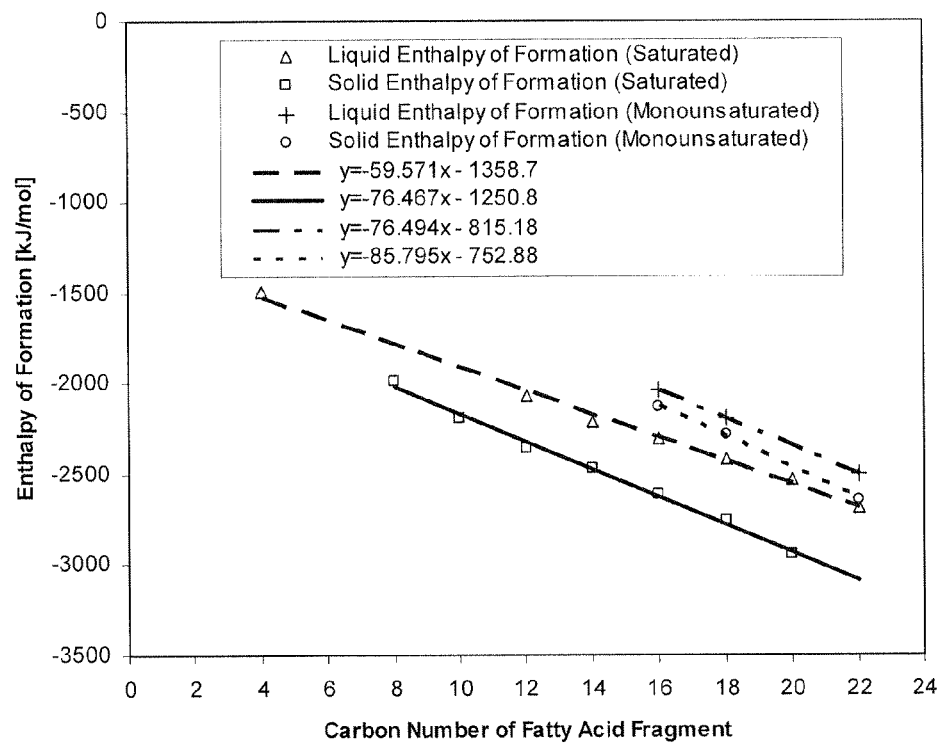
FIG. 7 is a graph of the relationship between enthalpy of formation for simple triglycerides and carbon numbers of the constituent fatty acids.
Figure 8:
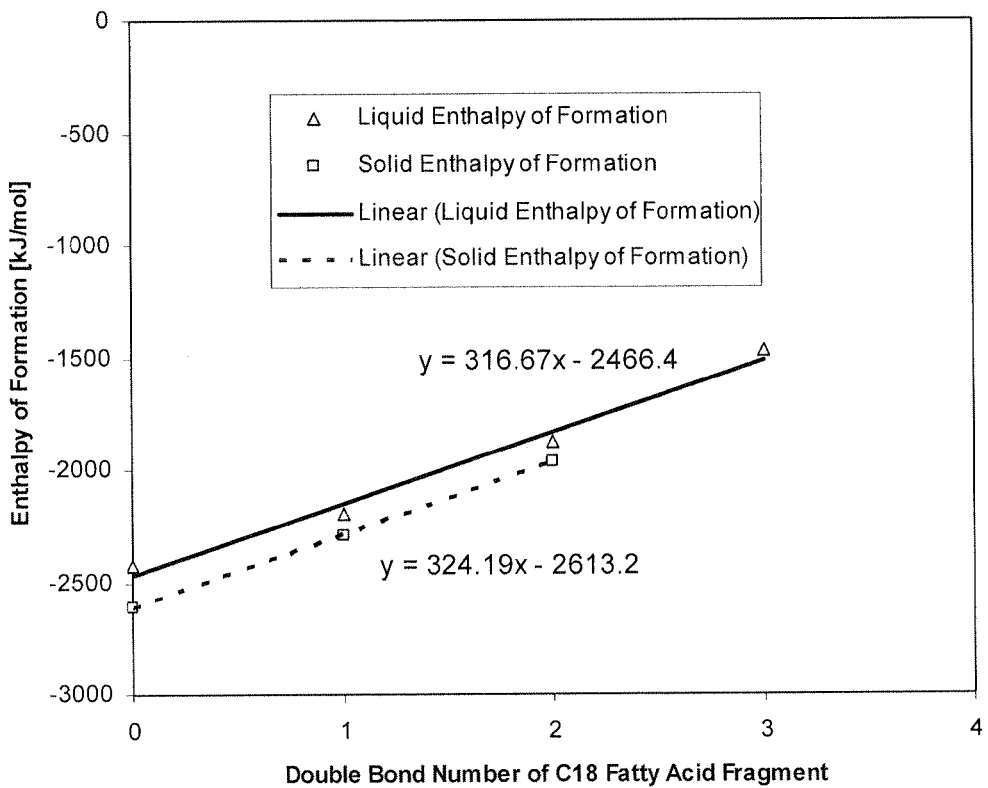
FIG. 8 is a graph of the relationship between enthalpy of formation and double bond number in C18 acid chains of simple triglycerides.

The relationships between enthalpy of formation for simple saturated and monounsaturated triglycerides and carbon numbers of the constituent fatty acids are illustrated in FIG. 7. The linear equations obtained by regression analysis, listed in FIG. 7, can then be used to extrapolate and predict enthalpies of formation for simple triglycerides composed of caproic acid (C6:0) and caprylic acid (C8:0). In addition, FIG. 8 correlates the enthalpy of formation to the double bond number in each acid chain of simple triglycerides including tristearin (C18:0), triolein (C18:1), trilinolein (C18:2) and trilinolenin (C18:3).

The enthalpy of formation for mixed triglycerides is calculated using the constituent fragment-based method by applying Eq. 13, which obtains the average of the values of standard enthalpy of formation of the simple triglycerides that make up the three fatty acid fragments $$\Delta H^\circ_{f,mix} = \sum \frac{n_A}{3} \Delta H^\circ_{f,A} \quad (13)$$

where
$\Delta H^\circ_{f,mix}$: Standard enthalpy of formation of the mixed triglyceride, (kJ/mol)
$\Delta H^\circ_{f,A}$: Standard enthalpy of formation of the simple triglyceride with fatty acid fragment A, (kJ/mol)
$n_A$: Number of the fatty acid fragment A in the mixed triglyceride.

Figure 9:
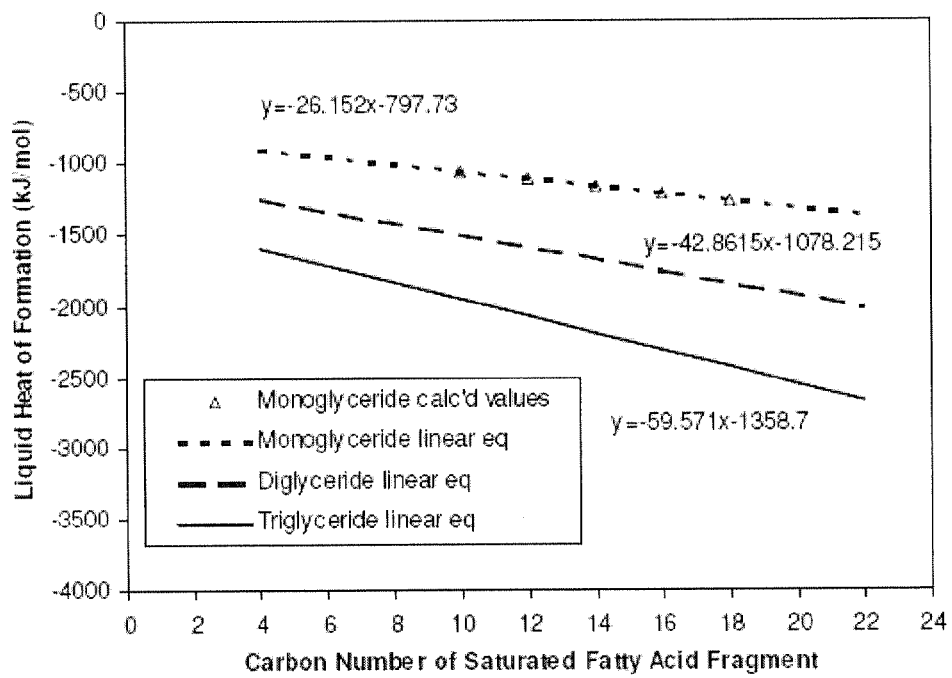
FIG. 9 is a graph of the relationship between liquid enthalpies of formation for mono-, di- and triglycerides and carbon number of the constituent fatty acids.

Liquid enthalpies of formation for monoglycerides including 1-monocaprin [C10:0], 1-monolaurin [C12:0], 1-monomyristin [C14:0], 1-monopalmitin [C16:0] and 1-monostearin [C18:0] are calculated from their solid enthalpies of formation. Silbert, L. S., Daubert, B. F., Mason, L. S., *The Heats of Combustion, Formation, and Isomerization of Isomeric Monoglycerides*, The Journal of Physical Chemistry, 69, 2887-2894 (1965). These calculated values for liquid enthalpies of formation are shown in FIG. 9. The linear relationship between liquid enthalpies of formation for monoglycerides and carbon numbers of the constituent fatty acids is plotted as the dotted line in FIG. 9. The linear equation yielded by regression analysis can then be used to extrapolate and predict liquid enthalpies of formation for monoglycerides composed of caproic acid [C6:0] and arachidic acid [C20:0] and so on. FIG. 9 also shows this relationship for simple triglycerides (see solid line). Applicants average out enthalpies of formation for the monoglycerides and the simple triglycerides with the same fatty acid fragments to represent the enthalpy of formation for the corresponding diglycerides. The dashed line in FIG. 9 plots the relationship between liquid enthalpy of formation for diglycerides and carbon numbers of the constituent fatty acids.

Based on the fragment approach, Applicants further estimate the enthalpy of formation for mixed diglycerides, i.e., diglycerides with two different fatty acid fragments using Eq. 14, which obtains the averages of the simple diglycerides with the two fatty acid fragments $$\Delta H^\circ_{f,mix} = \sum_A \frac{1}{2} \Delta H^\circ_{f,A} \quad (14)$$

where
$\Delta H^\circ_{f,mix}$: Standard enthalpy of formation of the mixed diglyceride, kJ/mol
$\Delta H^\circ_{f,A}$: Standard enthalpy of formation of the simple diglyceride with the fatty acid fragment A, kJ/mol.

Liquid Molar Volume

The liquid molar volume of a triglyceride component is calculated from the fragment composition and the fragment parameters:

$$V^l = N_{frag} \sum_A^{N_{frag}} x_A V_A^l(T) \quad (15)$$

where
$V_A^l$: Liquid molar volume of fragment A in the triglyceride component, (m³/kmol)
$N_{frag}$: Number of fragments in the triglyceride component
$x_A$: Mole fraction of fragment A in the triglyceride component.

The Van Krevelen model is used to estimate the liquid molar volume of fatty acid fragments. See Van Krevelen, D. W., *Properties of Polymers*. Amsterdam: Elsevier, 3rd ed., (1990). The liquid molar volume of fragment A is obtained from Eq. 16:

$$V_A^l = \frac{1 + B_{2,A} T}{B_{1,A}} \quad (16)$$

where
$B_{1,A}$ and $B_{2,A}$: Temperature dependency correlation parameters of fragment A
T: Temperature, (K).

Figure 10A:
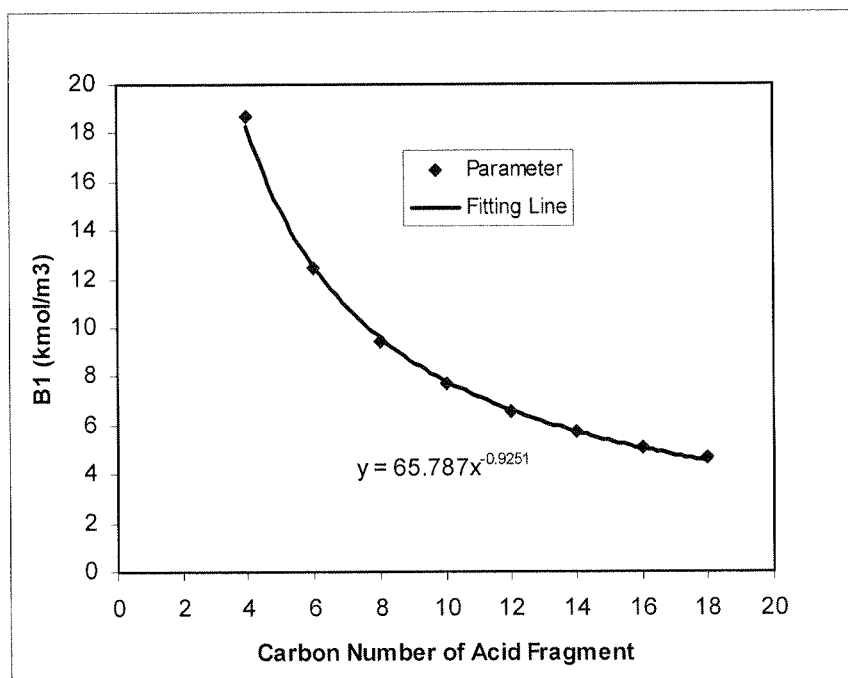
FIG. 10A is a graph of the relationship between fragment parameter $B_{1,A}$ and carbon number of each saturated acid fragment.
Figure 10B:
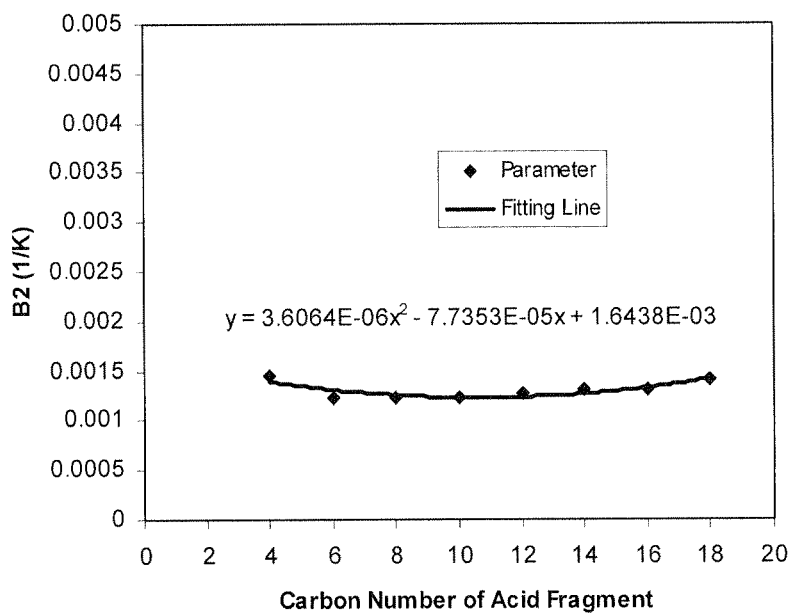
FIG. 10B is a graph of the relationship between fragment parameter $B_{2,A}$ and carbon number of each saturated acid fragment.

The parameters $B_{1,A}$ and $B_{2,A}$ for the glycerol fragment and saturated fatty acid fragments with carbon numbers ranging from 4 to 18 were obtained by regression against available literature experimental density data in a temperature range from 253.15 K to 516.15 K. See Nilsson, S.-O., Wadso, I., "Thermodynamic Properties of Some Mono-, Di-, and Tri-Esters. Enthalpies of Solution in Water at 288.15 to 318.15 K and Enthalpies of Vaporization and Heat Capacities at 298.15 K," *Journal of Chemical Thermodynamics*, 1986, 18, 673-681; Jaeger, F. M., "Temperature Dependence of the Free Surface Energy of Liquids in Temperature Range from −80 to 1650 degrees Centigrade," *Zeitschrift füer Anorganische and Allgemeine Chemie*, 101, 1-214 (1917); Phillips, J. C., Mattamal, G. J., "Effect of Number of Carboxyl Groups on Liquid Density of Esters of Alkylcarboxylic Acids," *Journal of Chemical and Engineering Data*, 23, 1-6 (1978). FIGS. 10A and 10B show the relationship between $B_{1,A}$ and $B_{2,A}$, respectively, and carbon number of each fatty acid fragment. The trend line equations are displayed on the chart of respective FIGS. 10A and 10B. The parameters of the saturated fragments with long chains, such as C20 and C22, can be extrapolated from the trend line equations.

Figure 11A:
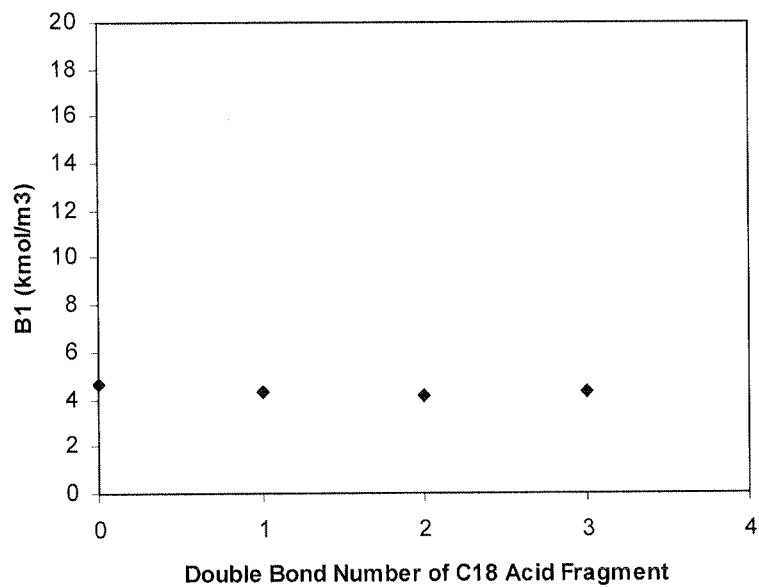
FIG. 11A is a graph of the relationship between fragment parameter $B_{1,A}$ and double bond number in C18 fatty acid fragments.
Figure 11B:
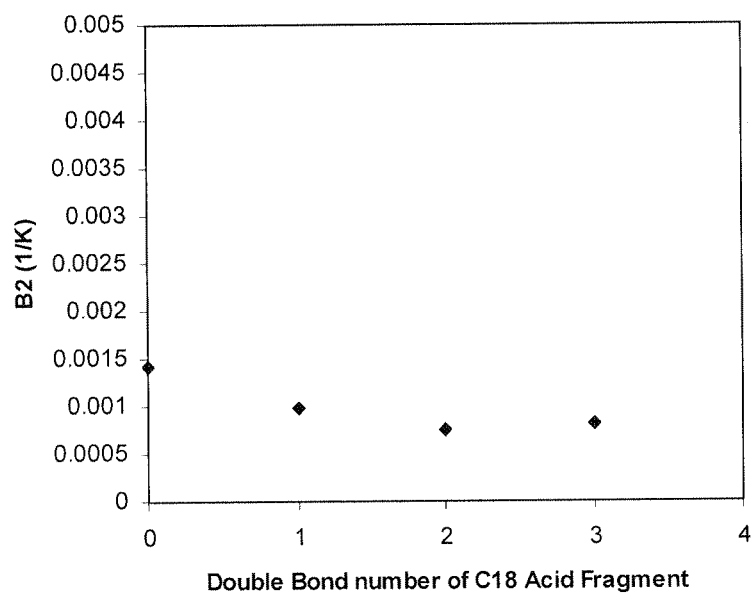
FIG. 11B is a graph of the relationship between fragment parameter $B_{2,A}$ and double bond number in C18 fatty acid fragments.

The parameters $B_{1,A}$ and $B_{2,A}$, of the oleic fragment (C18:1), the linoleic fragment (C18:2), and the linolenic fragment (C18:3) were obtained by regression against available literature experimental density data. See Sum, A. K., Biddy, M. J., de Pablo, J. J., "Predictive Molecular Model for the Thermodynamics and Transport Properties of Triacylglycerols," *Journal of Physical Chemistry B*, 107, 14443-14454 (2003); Jaeger, F. M., "Temperature Dependence of the Free Surface Energy of Liquids in Temperature Range from −80 to 1650 degrees Centigrade," *Zeitschrift füer Anorganische and Allgemeine Chemie*, 101, 1-214 (1917). FIGS. 11A and 11B graph $B_{1,A}$ and $B_{2,A}$, respectively, for the fatty acid fragment with carbon number 18 against double bond number. Table 7 summarizes the calculated parameters $B_{1,A}$ and $B_{2,A}$ for the glycerol fragment and fatty acid fragments with carbon numbers ranging from 4 to 22.

Figure 12:
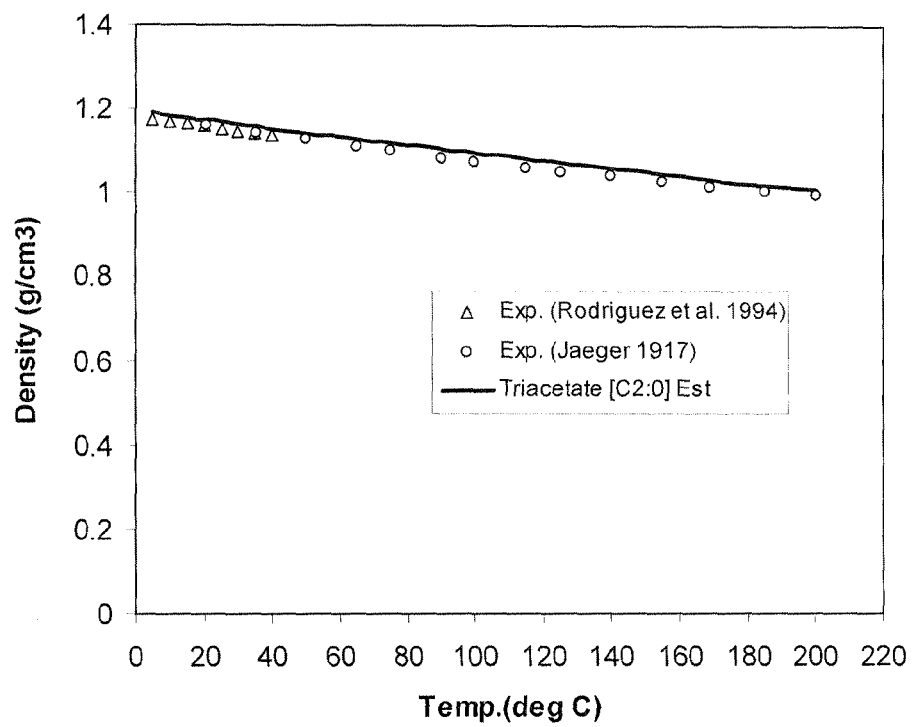
FIG. 12 is a graph of the predicted liquid density of triacetate, experimental data from Rodriguez et al., and Jaeger.

The parameters $B_{1,A}$ and $B_{2,A}$ for the monoglycerol fragment are regressed against experimental density data of monoacetate [C2:0] with a temperature range from 283.15 K to 343.15 K. Morgan, J. L. R., Chazal, P. M., "The Weight of a Falling Drop and the Laws of Tate, XV. The Drop Weights of Certain Organic Liquids and the Surface Tensions and Capillary Constants Calculated from Them," *Journal of the American Chemical Society*, 35, 1821-1834 (1913); Walden, P., Swinne, R., "The Capillary Constants of Liquid Esters," *Z. Phys. Chem.*, 77, 700-758 (1912). Note that the acetic acid fragment parameters are extrapolated from the relationships between the fragment parameters $B_{1,A}$, $B_{2,A}$ and the carbon number of the fatty acid fragments. FIG. 12 shows the densities of triacetate [C2:0] predicted by the fragment approach with the extrapolated acetic acid fragment parameters and the experimental density data. Rodriguez, M., Galan, M., Munoz, M. J., Martin, R., "Viscosity of Triglycerides+Alcohols from 278 to 313 K," *Journal of Chemical & Engineering Data*, 39, 102-105 (1994); Jaeger, F. M., "Temperature Dependence of the Free Surface Energy of Liquids in Temperature Range from −80 to 1650 Degrees Centigrade," *Zeitschrift füer Anorganische and Allgemeine Chemie*, 101, 1-214 (1917). The results show the predictions are in agreement with the experimental data. The parameters $B_{1,A}$ and $B_{2,A}$ for the diglycerol fragment are regressed against experimental density data of diacetate. Komandin, A. V., Rosolovskii, V. Y., "Densities and Molar Volumes of Some Organic Compounds over a Broad Temperature Range," *Zh. Fiz. Khim*, 33, 1280-1282 (1959).

TABLE 7

Calculated Liquid Molar Volume Fragment Parameters $B_{1,A}$ and $B_{2,A}$

| Fragments | Symbols | Carbons | $B_{1,A}$ (kmol/m³) | $B_{2,A}$ (1/K) * 10⁴ |
|---|---|---|---|---|
| Monoglycerol | | | 17.412 | 6.9785 |
| Diglycerol | | | 18.939 | 9.5032 |
| Triglycerol | Gly-frag | | 20.048 | 7.6923 |
| Butyric | Bu-frag | C4:0 | 18.650 | 14.503 |
| Caproic | Co-frag | C6:0 | 12.476 | 12.385 |
| Caprylic | Cy-frag | C8:0 | 9.3964 | 12.232 |
| Capric | C-frag | C10:0 | 7.6999 | 12.345 |
| Lauric | L-frag | C12:0 | 6.5791 | 12.687 |
| Myristic | M-frag | C14:0 | 5.7580 | 13.154 |
| Palmitic | P-frag | C16:0 | 5.0524 | 13.008 |
| Palmitoleic | Po-frag | C16:1 | 5.0524 | 13.008 |
| Stearic | S-frag | C18:0 | 4.6326 | 14.091 |
| Oleic | O-frag | C18:1 | 4.2924 | 9.8650 |
| Linoleic | Li-frag | C18:2 | 4.1679 | 7.4102 |
| Linolenic | Ln-frag | C18:3 | 4.3225 | 8.1078 |
| Arachidic | A-frag | C20:0 | 4.1168 | 15.393 |
| Behenic | B-frag | C22:0 | 3.7693 | 16.875 |
| Erucic | E-frag | C22:1 | 3.7693 | 16.875 |

Liquid Viscosity

Liquid viscosity of a triglyceride is calculated using the fragment composition and parameters of fragments:

$$\ln \eta^l = N_{frag} \sum_A^{N_{frag}} x_A \ln \eta_A^l(T) \quad (17)$$

where $\eta_A^l$: Liquid viscosity of fragment A in the triglyceride component, (Pa-s)

$N_{frag}$: Number of fragments in the triglyceride component $x_A$: Mole fraction of fragment A in the triglyceride component.

The following expression is used to represent liquid viscosity of fragment type A as a function of temperature:

$$\ln \eta_A^l = C_{1,A} + \frac{C_{2,A}}{T} + C_{3,A} \ln T \quad (18)$$

where $C_{1,A}$, $C_{2,A}$, and $C_{3,A}$: Temperature dependency correlation parameters T: Temperature, K.

See Reid, R. C., Prausnitz, J. M., Poling, B. E., *The Properties of Gases and Liquids*, New York: McGraw-Hill, 4th ed., 439 (1987).

Figure 13A:
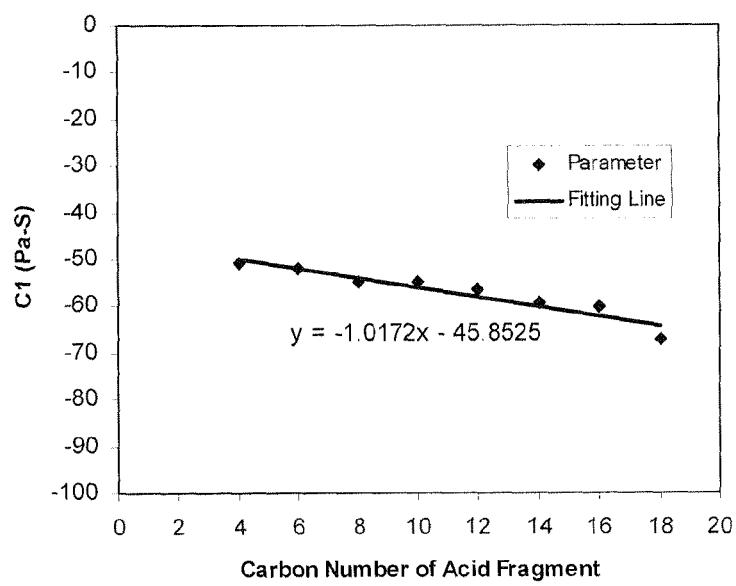
FIG. 13A is a graph of the relationship between viscosity parameter $C_{1,A}$ and carbon number of each saturated fatty acid fragment.
Figure 13B:
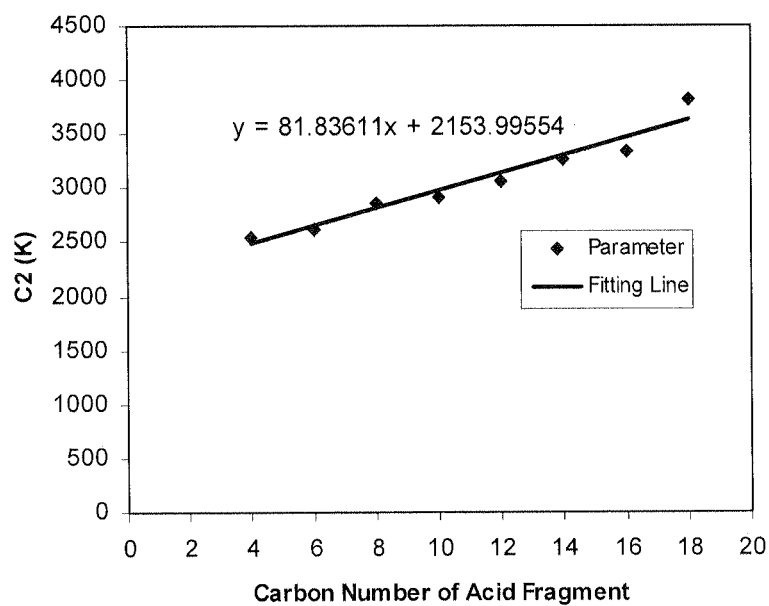
FIG. 13B is a graph of the relationship between viscosity parameter $C_{2,A}$ and carbon number of each saturated fatty acid fragment.
Figure 13C:
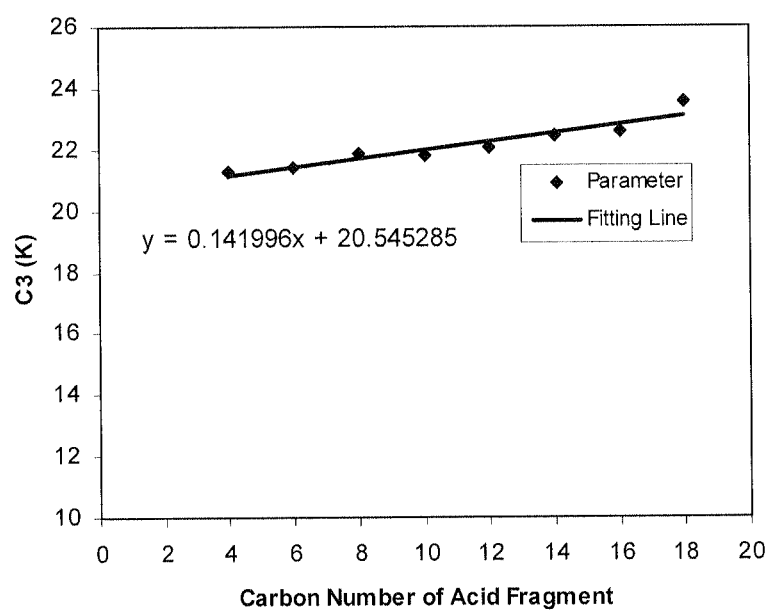
FIG. 13C is a graph of the relationship between viscosity parameter $C_{3,A}$ and carbon number of each saturated fatty acid fragment.

The parameters $C_{1,A}$, $C_{2,A}$, and $C_{3,A}$ for the glycerol fragment and saturated fatty acid fragments with carbon numbers ranging from 4 to 18 were obtained by regression against available experimental viscosity literature data with a temperature range of 298.15 K to 516.15 K. See Rodriguez, M., Galan, M., Munoz, M. J., Martin, R., "Viscosity of Triglycerides+Alcohols from 278 to 313 K," *Journal of Chemical and Engineering Data*, 39, 102-105 (1994); Kishore, K., Shobha, H. K., Mattamal, G. J., "Structural Effects on the Vaporization of High Molecular Weight Esters," *Journal of Physical Chemistry*, 94, 1642-1648 (1990); Niir, B., *Modern Technology of Oils, Fats and Its Derivatives*. New Delhi: National Institute of Industrial Research, 9-11 (2000). FIGS. 13A-C illustrate the relationships between the $C_{1,A}$, $C_{2,A}$, and $C_{3,A}$, parameters and carbon number of each fatty acid fragment. The parameters for the saturated fragments with long chains, such as C20 and C22, can be extrapolated from the linear equations on the respective figure's chart shown in FIGS. 13A, 13B, and 13C, respectively.

Figure 14A:
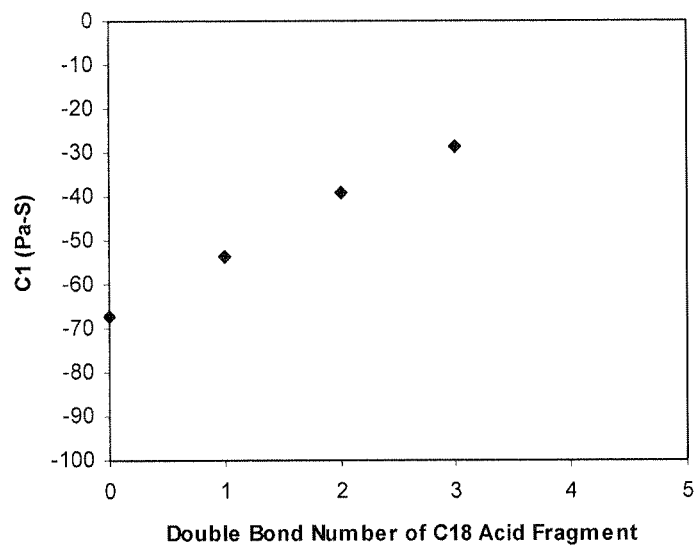
FIG. 14A is a graph of the relationship between viscosity fragment parameter $C_{1,A}$ and double bond number in C18 fatty acid fragments.
Figure 14B:
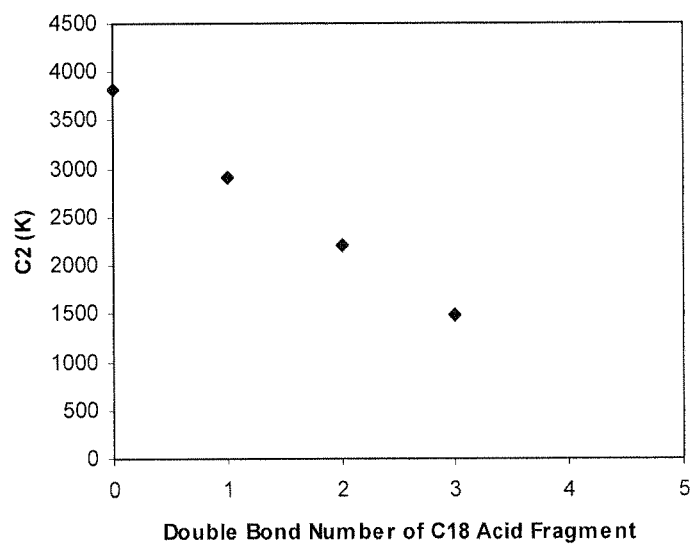
FIG. 14B is a graph of the relationship between viscosity fragment parameter $C_{2,A}$ and double bond number in C18 fatty acid fragments.
Figure 14C:
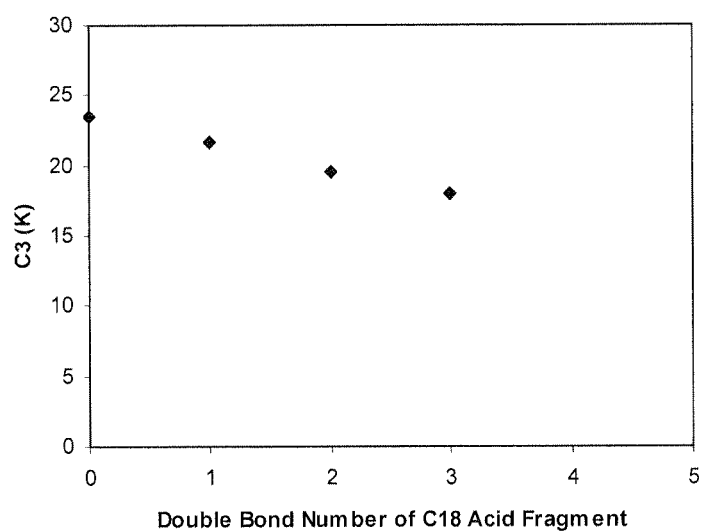
FIG. 14C is a graph of the relationship between viscosity fragment parameter $C_{3,A}$ and double bond number in C18 fatty acid fragments.

The effect of double bond number of each fatty acid fragment on the viscosity parameters of the oleic fragment (C18:1), the linoleic fragment (C18:2) and the linolenic fragment (C18:3) were obtained by regression against literature experimental data. See Ceriani, R., Goncalves, C. B., Rabelo, J., Caruso, M., Cunha, A. C. C., Cavaleri, F. W., Batista, E. A. C., Meirelles, A. J. A., "Group Contribution Model for Predicting Viscosity of Fatty Compounds," *Journal of Chemical and Engineering Data*, 52, 965-972 (2007); Eduljee, G. H., Boyes, A. P., "Viscosity of Some Binary Liquid Mixtures of Oleic Acid and Triolein with Selected Solvents," *Journal of Chemical and Engineering Data*, 25, 249-252 (1980); Exarchos, N. C., Tasioula-Margari, M., Demetropoulos, I. N., "Viscosities and Densities of Dilute Solutions of Glycerol Trioleate+Octane, +P-xylene, +Toluene, and +Chloroform," *Journal of Chemical and Engineering Data*, 40, 567-571 (1995); Valeri, D., Meirelles, A. J. A., "Viscosities of Fatty Acids, Triglycerides, and Their Binary Mixtures." *Journal of the American Oil Chemists' Society*, 74, 1221-1226 (1997). FIGS. 14A-C illustrate the relationship between viscosity parameters and double bond number for the fatty acid fragment with carbon number 18. Table 8 summarizes the calculated parameters $C_{1,A}$, $C_{2,A}$, and $C_{3,A}$, for the glycerol fragment and fatty acid fragments with carbon numbers ranging from 4 to 22.

Liquid viscosities of mono- and diglycerides are not included here due to the lack of necessary experimental data.

TABLE 8

Calculated Liquid Viscosity Fragment Parameters $C_{1,A}$, $C_{2,A}$, and $C_{3,A}$

| Fragments | Symbols | Carbons | $C_{1,A}$ (Pa-s) | $C_{2,A}$ (K) | $C_{3,A}$ (K) |
|---|---|---|---|---|---|
| Glycerol | Gly-frag | | 96.530 | −3009.6 | −57.439 |
| Butyric | Bu-frag | C4:0 | −51.003 | 2546.1 | 21.264 |
| Caproic | Co-frag | C6:0 | −51.864 | 2627.6 | 21.387 |
| Caprylic | Cy-frag | C8:0 | −55.104 | 2867.5 | 21.843 |
| Capric | C-frag | C10:0 | −54.786 | 2919.1 | 21.784 |
| Lauric | L-frag | C12:0 | −56.622 | 3060.8 | 22.045 |
| Myristic | M-frag | C14:0 | −59.334 | 3259.8 | 22.425 |
| Palmitic | P-frag | C16:0 | −60.312 | 3339.1 | 22.567 |
| Palmitoleic | Po-frag | C16:1 | −60.312 | 3339.1 | 22.567 |
| Stearic | S-frag | C18:0 | −67.306 | 3813.5 | 23.543 |
| Oleic | O-frag | C18:1 | −53.789 | 2911.7 | 21.653 |
| Linoleic | Li-frag | C18:2 | −39.270 | 2216.4 | 19.488 |
| Linolenic | Ln-frag | C18:3 | −28.757 | 1491.5 | 18.027 |
| Arachidic | A-frag | C20:0 | −66.197 | 3790.7 | 23.385 |
| Behenic | B-frag | C22:0 | −68.231 | 3954.4 | 23.669 |
| Erucic | E-frag | C22:1 | −68.231 | 3954.4 | 23.669 |

In embodiments, a biodiesel production modeling system 100 (FIG. 15) includes a data store 99 holding a plurality of triglyceride physical property values obtained by, for each of different triglycerides, i) estimating values of a physical property of constituent fatty acid fragments of the triglyceride, and ii) computing the physical property of the triglyceride by expressing a value of the physical property of the triglyceride as a sum of the estimated values of the physical property of constituent fatty acid fragments of the triglyceride. Similarly, mono- and diglyceride data (physical property values of constituent fatty acid fragments) can be indexed and stored in one or more data stores 99 together with or separate from triglyceride data. The system 100 further includes a modeler (or modeling engine) 91 that uses the computed mono-, di-, and triglyceride physical property values stored in the data store 99 to determine a value of the physical property of a biodiesel feedstock. The modeler 91 expresses the value of the physical property of the biodiesel feedstock as a sum of values from the stored and computed mono-, di-, and triglyceride physical property values corresponding to constituent mono-, di-, and triglycerides of the biodiesel feedstock.

The data store 99 is configured to be searchable, indexed by triglyceride component name, molecule shorthand, fatty acid acronym and/or the like. Relational databases or other databases can be used to implement data store 99. It is understood that other configurations and implementations of data store 99 are suitable.

Figure 15:
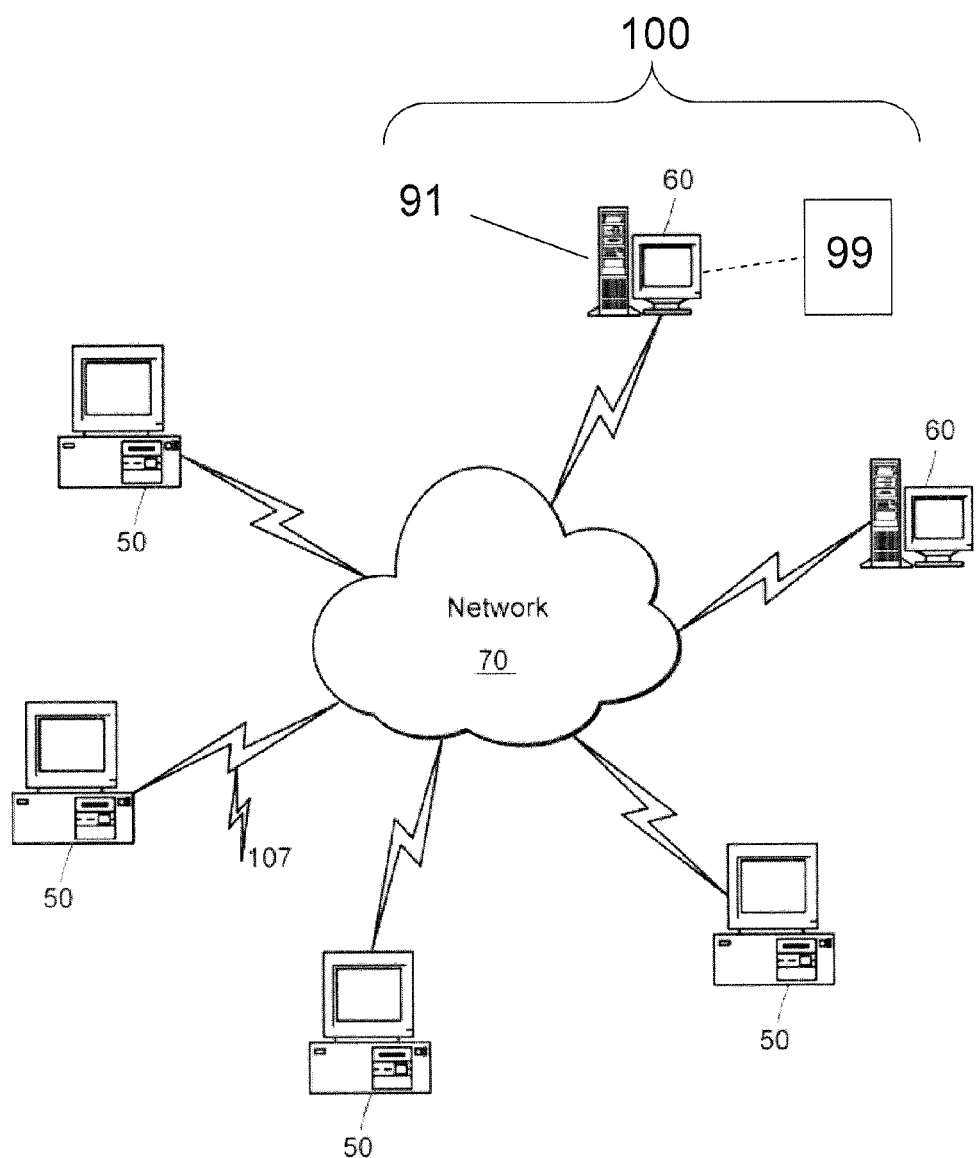
FIG. 15 is a schematic view of a computer network in which embodiments of the present invention are implemented.

FIG. 15 illustrates a computer network or similar digital processing environment in which the present invention can be implemented. Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 16:
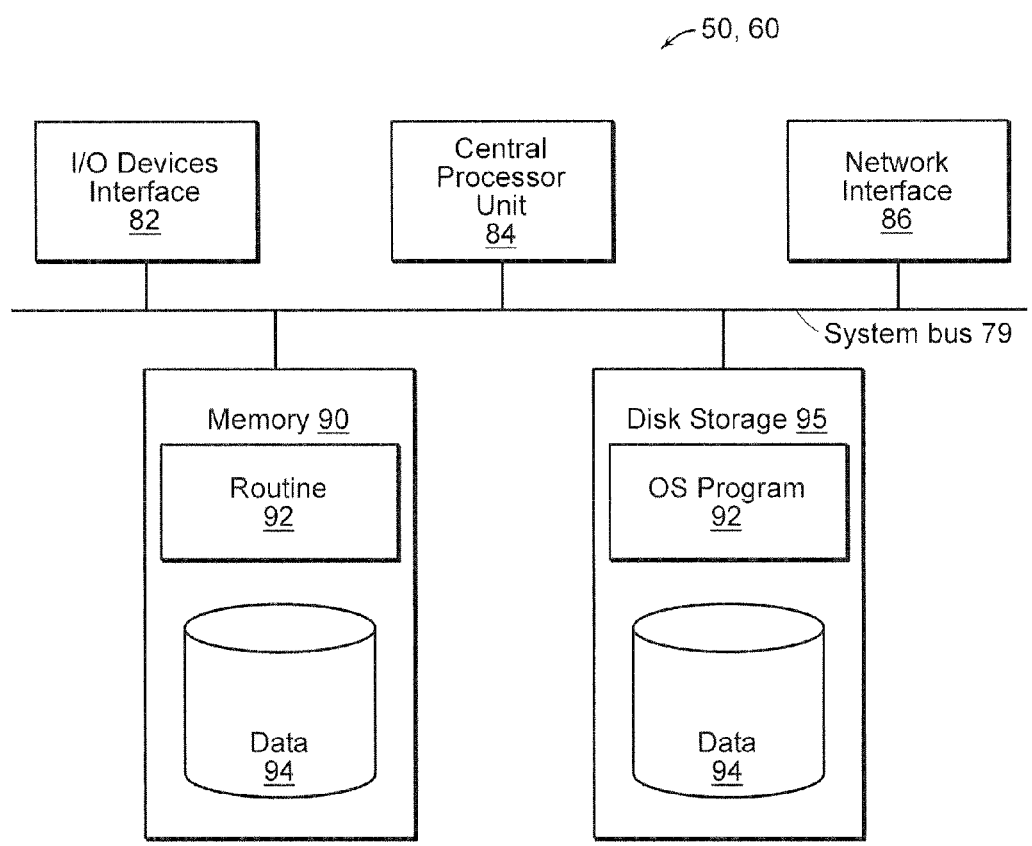
FIG. 16 is a block diagram of a computer node in the network of FIG. 15.

FIG. 16 is a diagram of the internal structure of a computer (e.g., client processor/device 50 or server computers 60) in the computer system of FIG. 15. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 11). Memory 90 provides volatile storage for computer software instructions 92 and data 94 used to implement an embodiment of the present invention (e.g., modeling engine 91, data store 99, and supporting modules or process code detailed below in FIG. 32). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions can also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal can be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 can receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Figure 32:
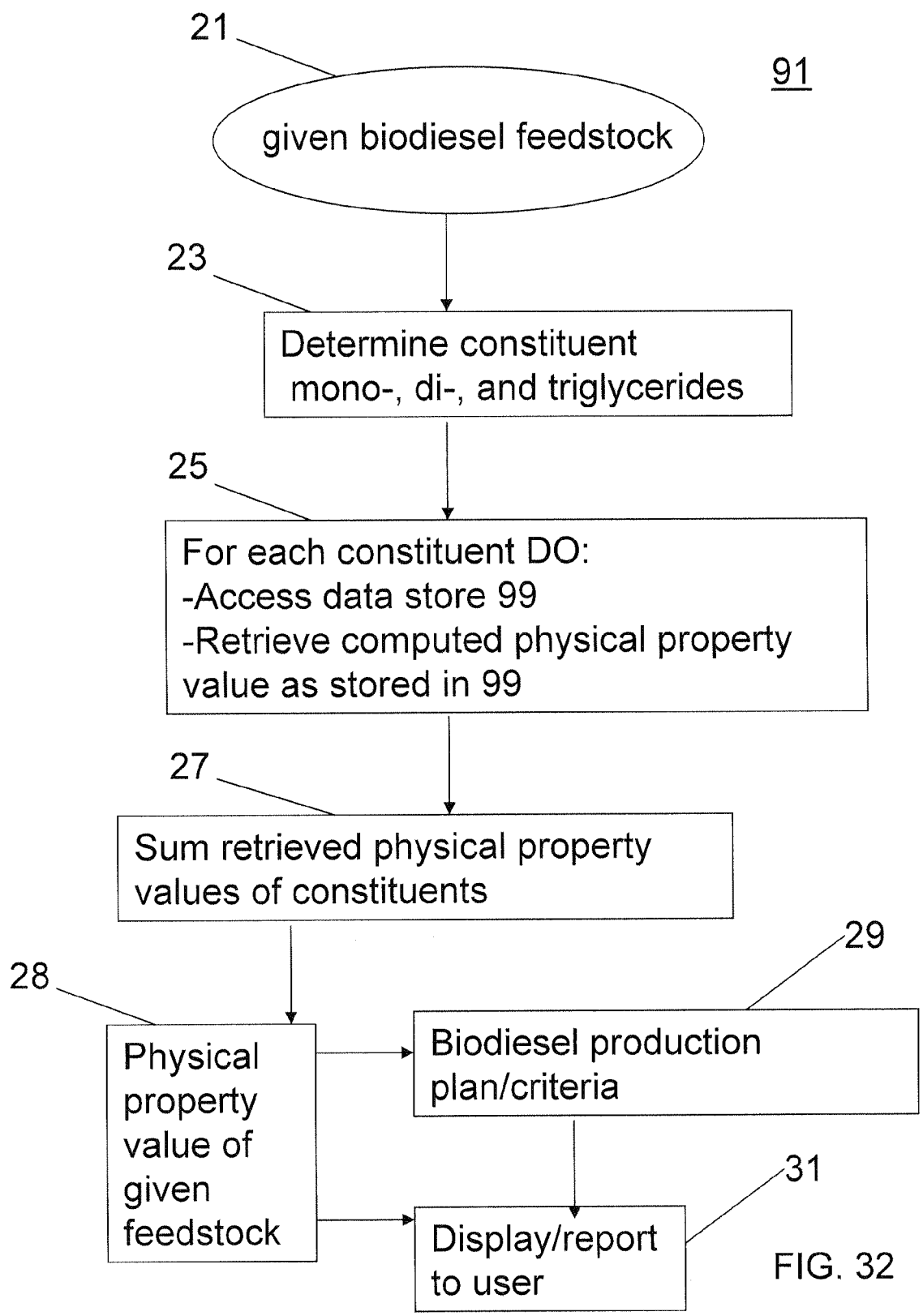
FIG. 32 is a flow diagram of one embodiment of the present invention.

With reference to FIG. 32, processing and data flow of modeler 91 in one embodiment are shown. At 21, a biodiesel feedstock (description or other indication thereof) is received as input to modeling engine 91. In response, step 23 determines the constituent mono-, di-, and/or triglycerides of the input feedstock of 21.

For each determined constituent, step 25 retrieves a physical property value by (a) accessing data store 99 using the constituent as an index, and (ii) obtaining the computed physical property value as stored in the data store 99.

The modeler 91 at step 27 sums the retrieved computed physical property values of the constituents, i.e., the physical property values produced by step 25. This results in a physical property value 28 of the input (given) feedstock. These results can be reported or otherwise output to a user 31. In a preferred embodiment, results 28 (i.e., the calculated physical property value of given feedstock) are utilized by a biodiesel production planner 29 or the like.

In particular, biodiesel production planner 29 compares the calculated physical property value 28 with criteria or threshold values. From the comparison, if the comparison biodiesel production planner 29 determines that the calculated physical property value 28 is outside of an acceptable range, then biodiesel production planner module 29 adjusts the input feedstock at 21 (by inputting other feedstock or a blend of feedstock for example). The modeling process 91 then repeats with the adjusted feedstock constituents.

From the comparison, if the biodiesel production planner 29 accepts the calculated physical property value 28 or otherwise qualifies the given input feedstock 21 as acceptable, then modeler 91 outputs an indication to user 31. The given input feedstock 21 (or resulting blend) is then used/useable in biodiesel production.

Figure 17:
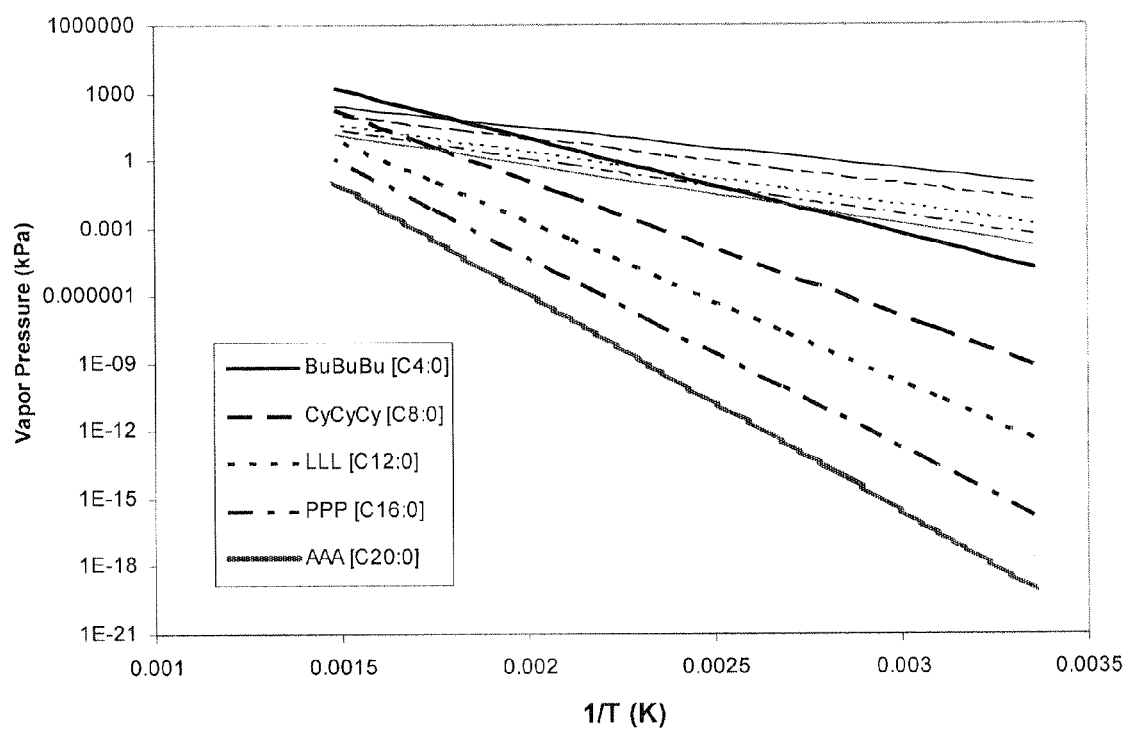
FIG. 17 is a graph of a comparison of predicted vapor pressure of simple saturated triglycerides; heavy-black lines are predictions with the fragment method, and light-black lines are predicted with the group contribution method; lines with the same legend corresponding to the same triglycerides.

Exemplification
Comparisons of Estimates of Triglyceride Pure Component Properties
Vapor Pressure The predicted results of vapor pressure for five simple saturated triglycerides are shown in FIG. 17. Heavy-black lines show the vapor pressure of triglycerides as predicted with the fragment approach. Light-black lines are the results as predicted by the Li-Ma functional group contribution method. See Li, P., Ma, P.-S., Yi, S.-Z., Zhao, Z.-G., Cong, L.-Z., "A New Corresponding-States Group-Contribution Method (CSGC) for Estimating Vapor Pressure of Pure Compounds," *Fluid Phase Equilibria*, 1994, 101, 101-119. As shown in FIG. 17, vapor pressures predicted by the Li-Ma functional group method are too large by several orders of magnitude. The values obtained from the constituent fragment-based method for carbon numbers 4 to 16 are obtained by regression of available experimental data. Therefore, the results from the constituent fragment-based approach shown in FIG. 17 and FIGS. 18-20 below are essentially the same as the available experimental data.

Heat Capacity

Figure 18:
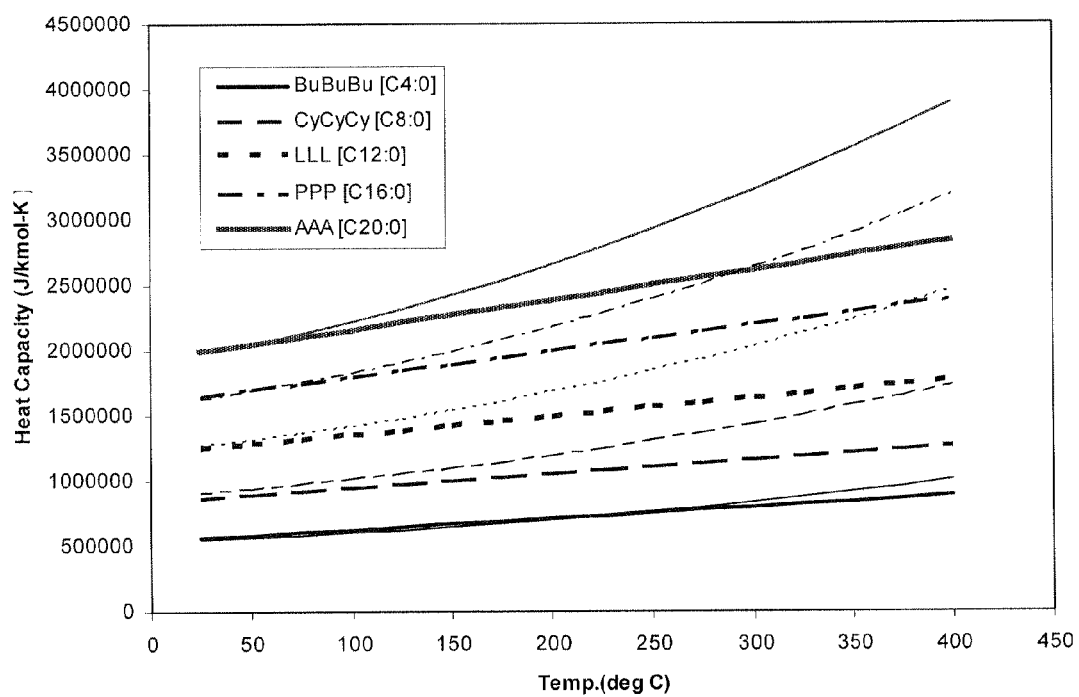
FIG. 18 is a graph of a comparison of predicted liquid heat capacity of simple saturated triglycerides; heavy-black lines are predictions with the fragment method, and light-black lines are predicted with the group contribution method; lines with the same legend corresponding to the same triglycerides.

FIG. 18 shows the predicted results (heavy-black lines) of liquid heat capacity for five simple saturated triglycerides with the constituent fragment-based method. Also shown are the predicted results (light-black lines) from the Ruzicka group contribution method. See Ruzicka, V. Jr., Domalski, E. S., "Estimation of the Heat Capacities of Organic Liquids as a Function of Temperature Using Group Additivity. I. Hydrocarbon Compounds," *Journal of Physical and Chemical Reference Data*, 22, 597-618 (1993); Ruzicka, V. Jr., Domalski, E. S., "Estimation of the Heat Capacities of Organic Liquids as a Function of Temperature Using Group Additivity. II. Compounds of Carbon, Hydrogen, Halogens, Nitrogen, Oxygen, and Sulfur," *Journal of Physical and Chemical Reference Data*, 22, 619-657 (1993). Heat capacities predicted by the Ruzicka functional group method are relatively close to the results calculated with the fragment-based method.

Liquid Density

Figure 19:
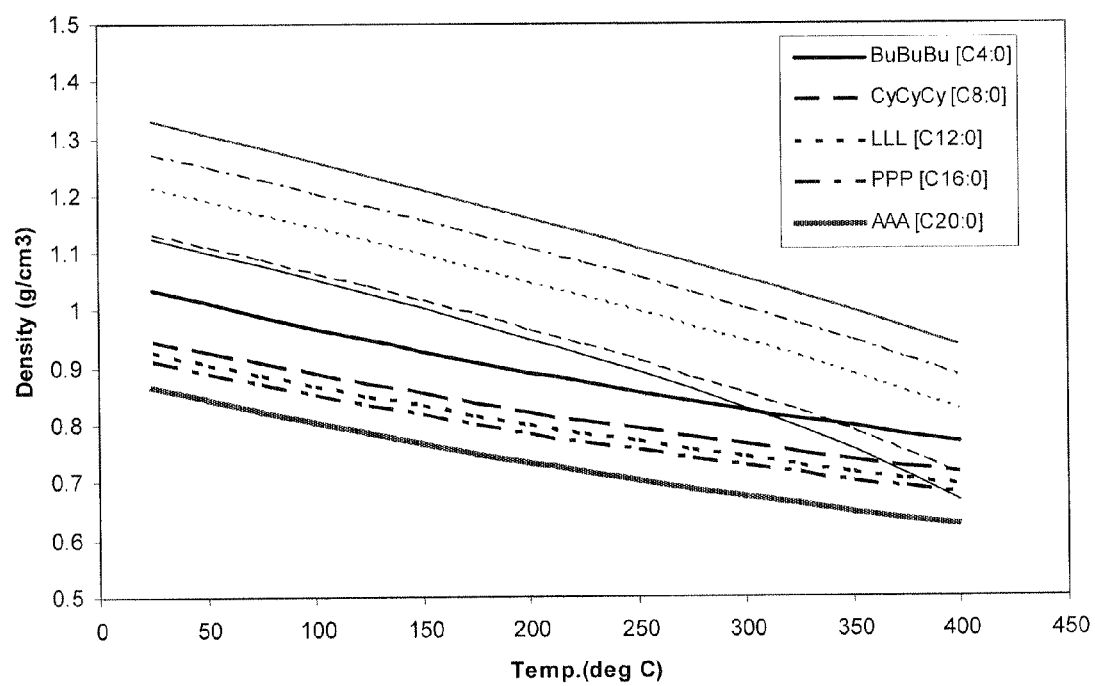
FIG. 19 is a graph of a comparison of predicted liquid density of simple saturated triglycerides; heavy-black lines are predictions with the fragment method, and light-black lines are predicted with the group contribution method; lines with the same legend corresponding to the same triglycerides.

FIG. 19 shows the predicted results of liquid density for five prevalent simple saturated triglycerides. Heavy-black lines show the liquid densities of the triglycerides as predicted with the fragment approach. Also shown are the prediction results from the Le Bas group contribution method (light-black lines). See Poling, B. E., Prausnitz, J. M., O'Connell, J. P., *The Properties of Gases and Liquids*, New York: McGraw-Hill Companies, 5th ed., 4.33 and 9.59-9.61 (2000). As shown in FIG. 19, densities predicted by the Le Bas group contribution method are approximately 30% too large.

Liquid Viscosity

Figure 20:
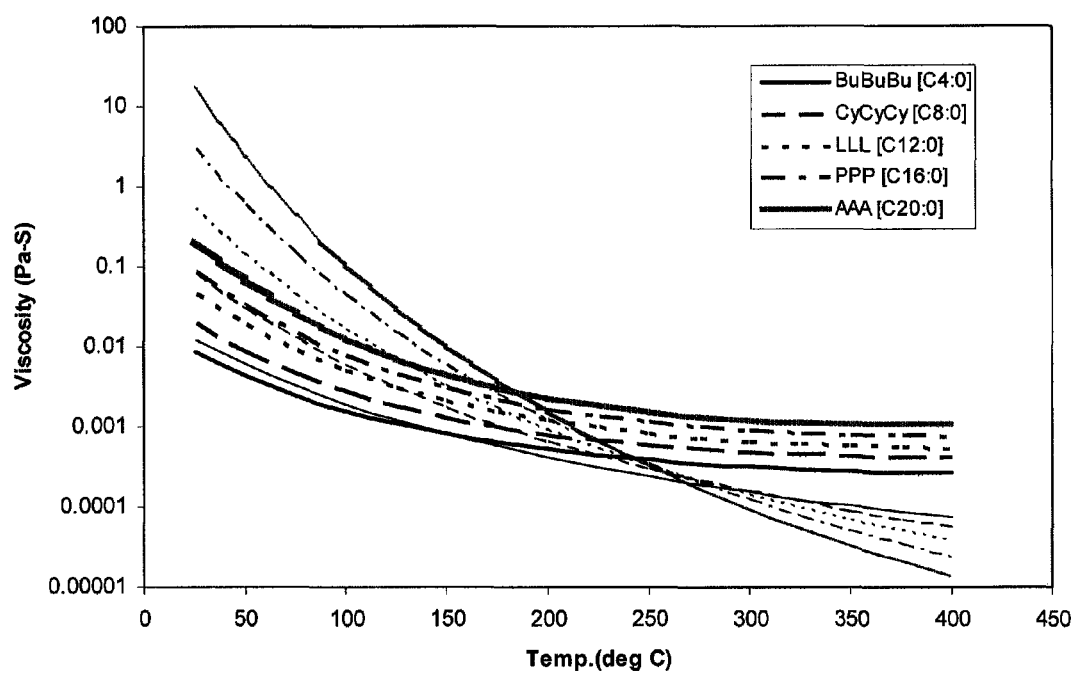
FIG. 20 is a graph of a comparison of predicted liquid viscosity of simple saturated triglycerides; heavy-black lines are predictions with the fragment method, and light-black lines are predicted with the group contribution method; lines with the same legend corresponding to the same triglycerides.

FIG. 20 shows the predicted results (heavy-black lines) of liquid viscosity for five prevalent simple saturated triglycerides. Also shown are the prediction results (light-black lines) with the Orrick-Erbar group contribution method. See Poling, B. E., Prausnitz, J. M., O'Connell, J. P., *The Properties of Gases and Liquids*, New York: McGraw-Hill Companies, 5th ed., 4.33 and 9.59-9.61 (2000). As shown in FIG. 20, viscosities predicted by the Orrick-Erbar method are orders of magnitude too large at temperatures of less than about 423.15 K and too small at temperatures above about 473.15 K.

Comparisons of Estimates of Mono- and Diglyceride Pure Component Properties

Figure 21A:
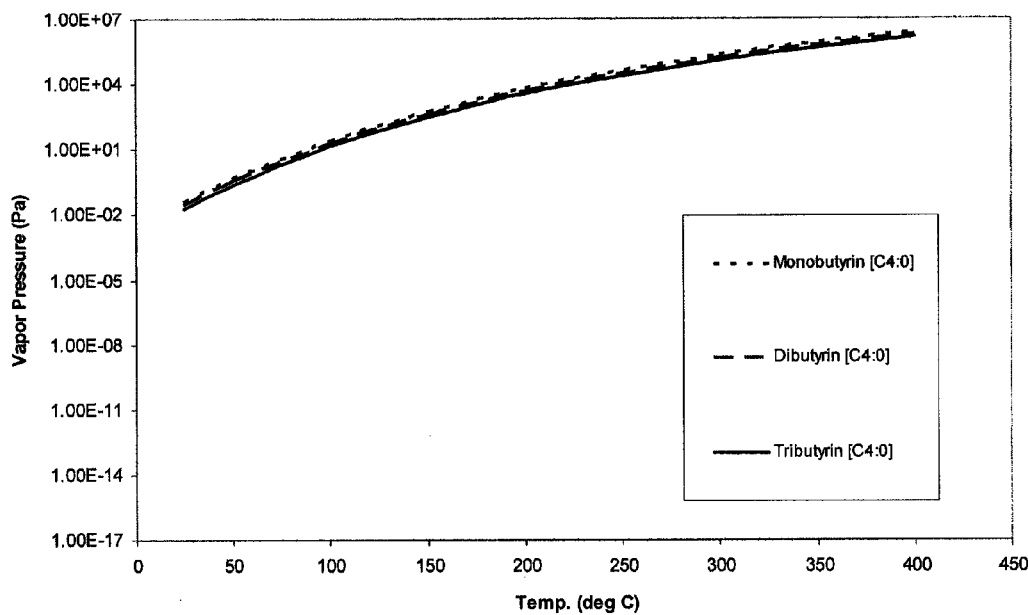
FIGS. 21A-C are graphs of comparisons of predicted vapor pressure of mono-, simple di- and triglycerides of (A) butyric, (B) lauric, and (C) arachidic acid; solid lines are triglycerides, dashed lines are diglycerides, dotted lines are monoglycerides.
Figure 21B:
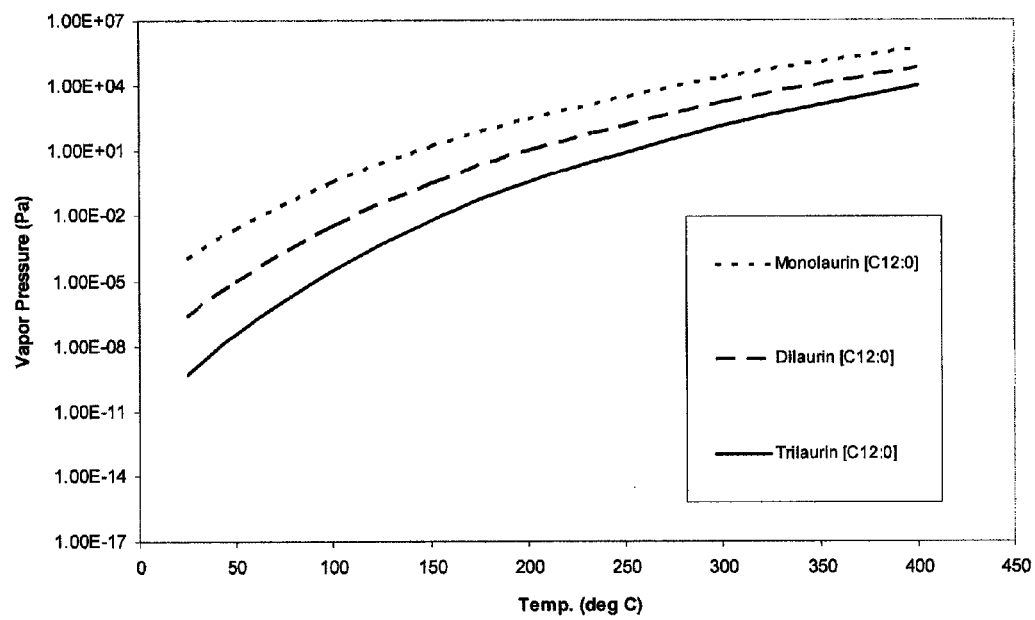
Figure 21C:
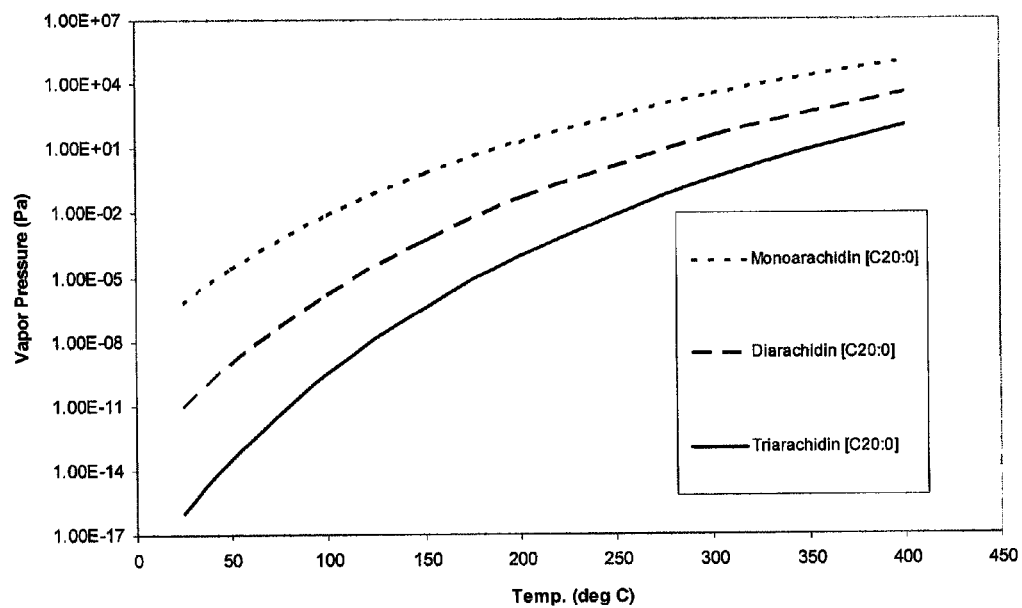
Figure 22A:
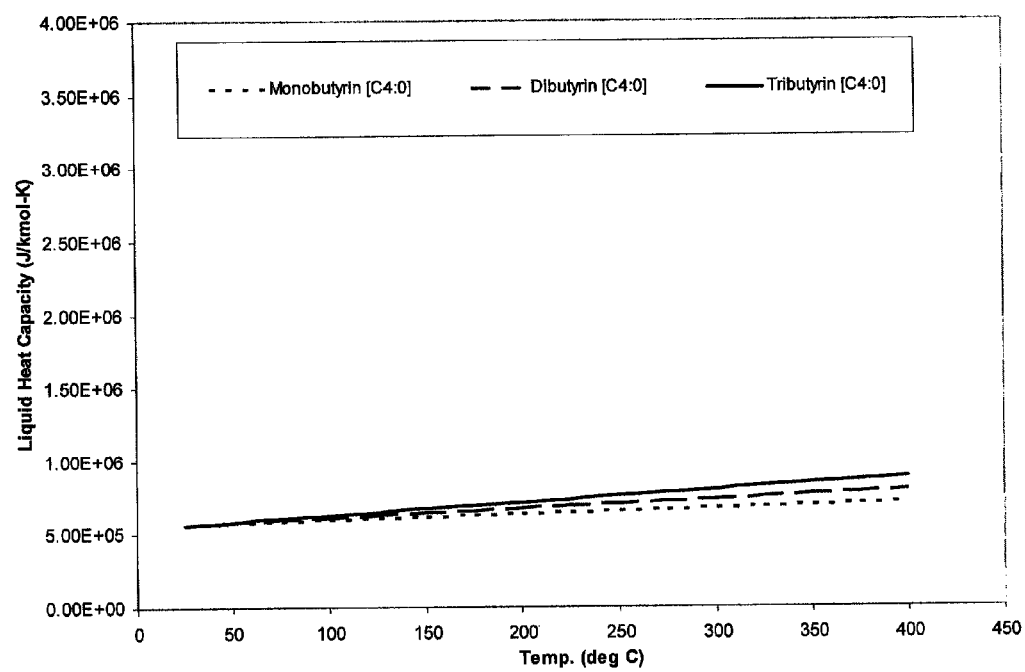
FIGS. 22A-C are graphs of comparisons of predicted liquid heat capacity of mono-, simple di- and triglycerides of (A) butyric, (B) lauric, and (C) arachidic acid; solid lines are triglycerides, dashed lines are diglycerides, dotted lines are monoglycerides.
Figure 22B:
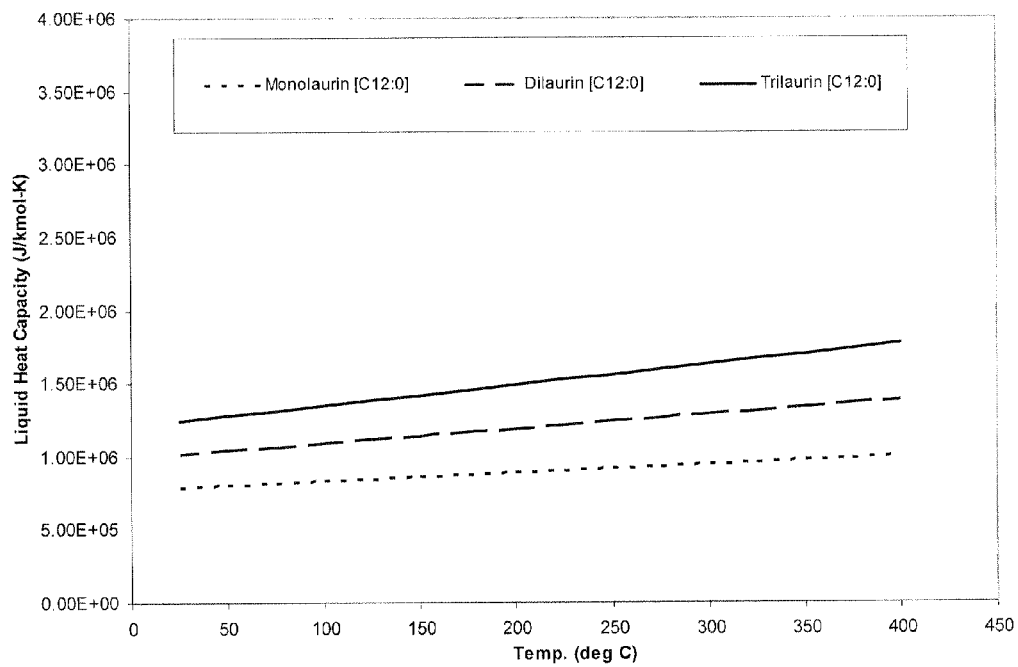
Figure 22C:
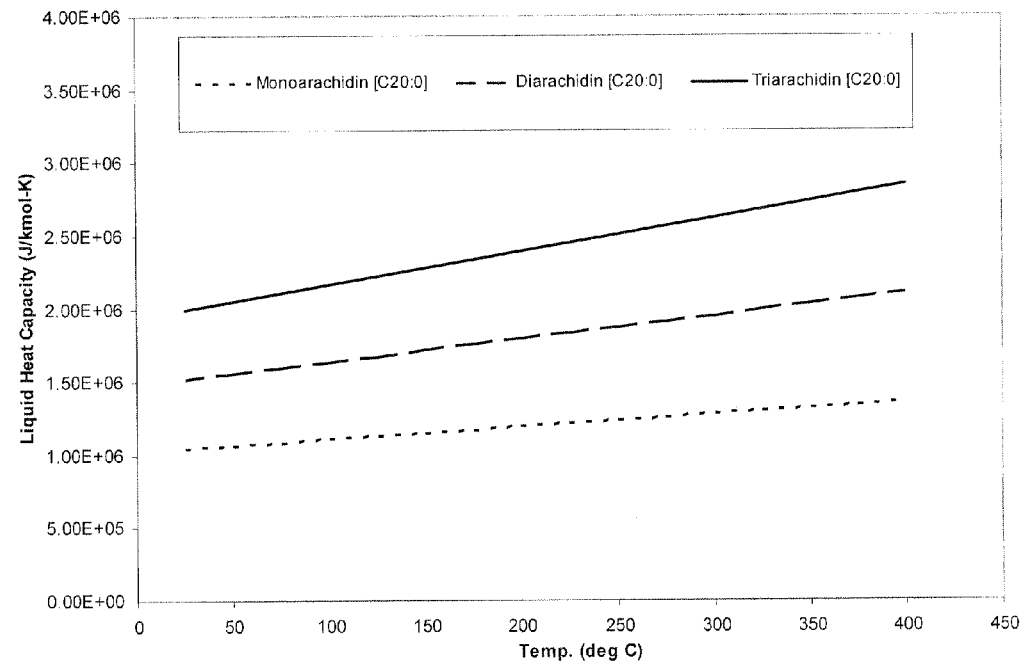
Figure 23A:
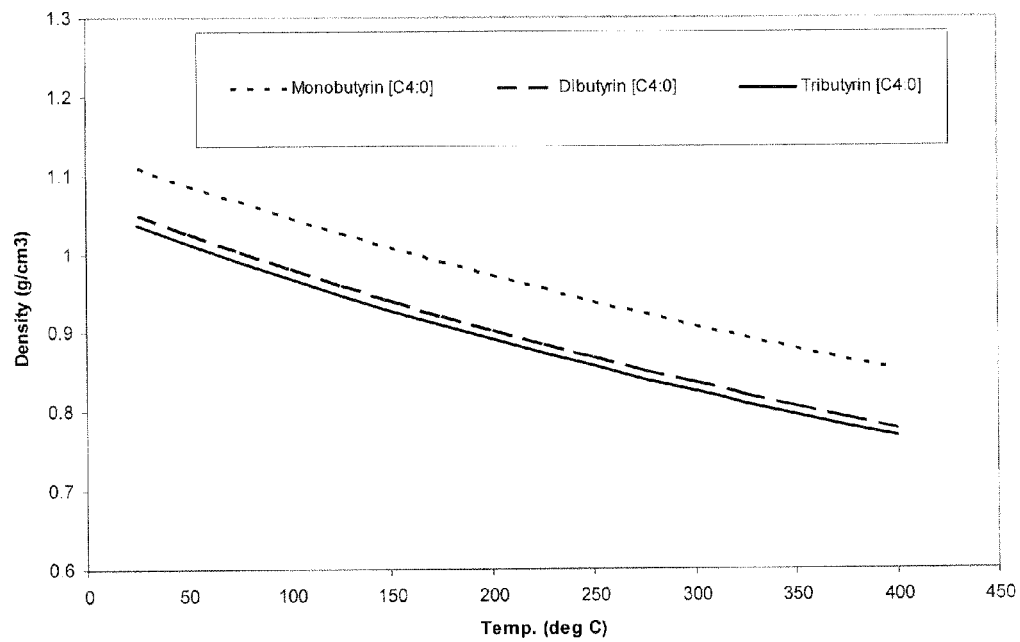
FIGS. 23A-C are graphs of comparisons of predicted density of mono-, simple di- and triglycerides of (A) butyric, (B) lauric, and (C) arachidic acid; solid lines are triglycerides, dashed lines are diglycerides, dotted lines are monoglycerides.
Figure 23B:
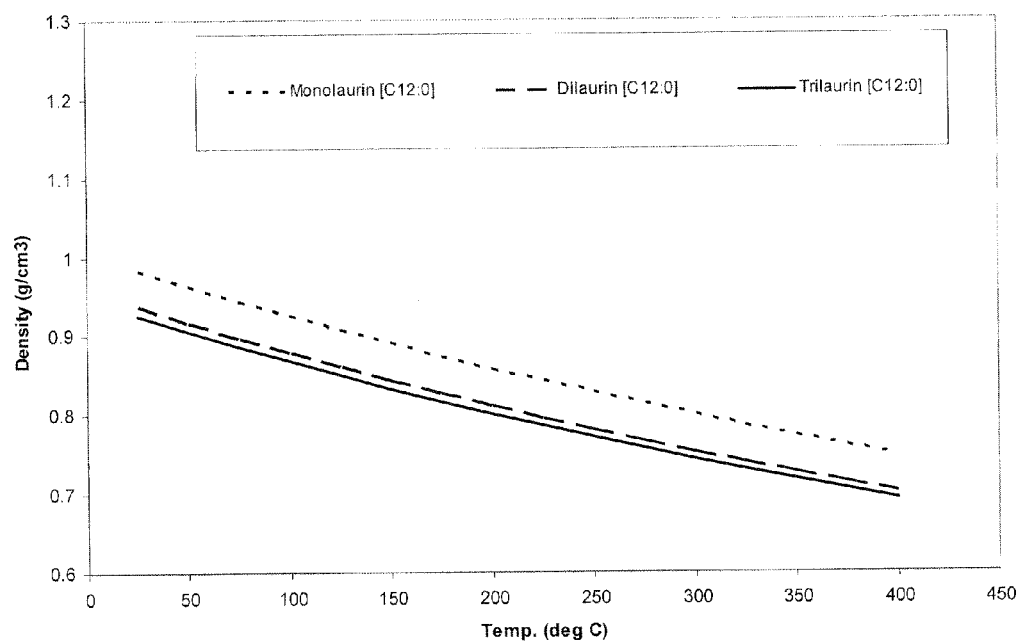
Figure 23C:
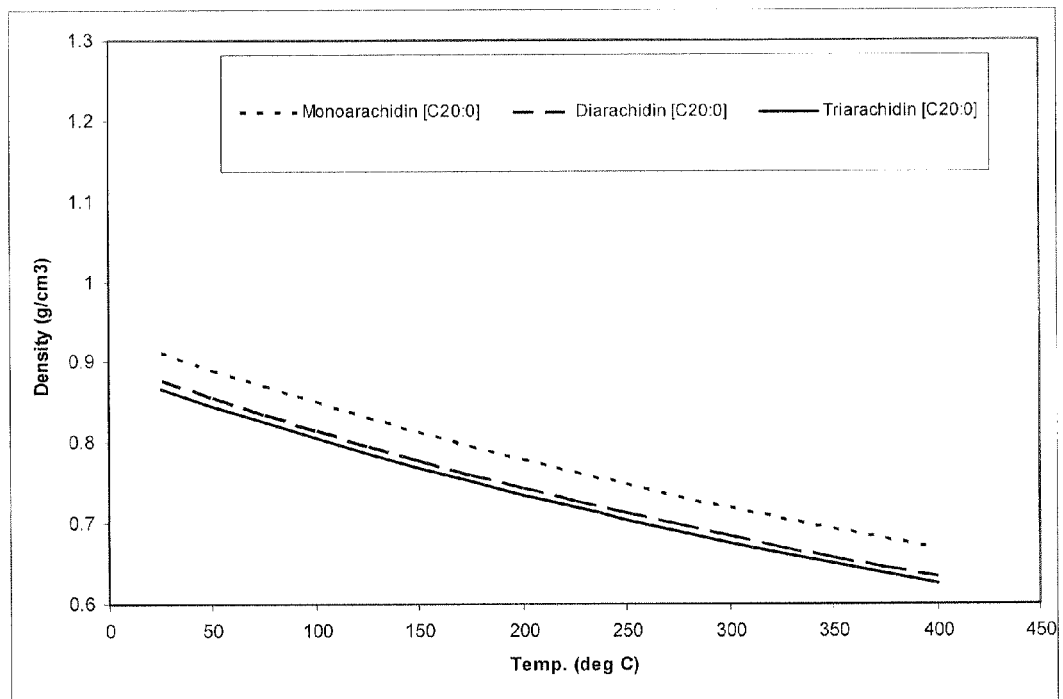

FIGS. 21-23 show the predicted results of vapor pressure, liquid heat capacity and liquid density for monoglycerides, simple diglycerides and simple triglycerides composed of butyric (C4), lauric (C12), and arachidic (C20) fatty acid fragments. Solid lines show the predictions of triglycerides. Dashed lines are the predictions of diglycerides. Dotted lines are the predictions of monoglycerides. The mono-, di- and triglycerides composed of the butyric fatty acid fragment are plotted in FIGS. 21-23A. The mono-, di- and triglycerides composed of the lauric fatty acid fragment are plotted in FIGS. 21-23B. The mono-, di- and triglycerides composed of the arachidic fatty acid fragment are plotted in FIGS. 21-23C.

As shown in FIGS. 21-23, with the increase of carbon number of mono- and diglycerides, the trends are similar to triglycerides. At the same temperature, the predicted vapor pressures of mono-, di- and triglycerides with the same fatty acid fragment decrease successively. The gaps among them enlarge with the increment of carbon number of the constituent fatty acid fragment. The predicted heat capacities of mono-, di- and triglycerides with the same fatty acid fragment rise in order at the same temperature. The differences among them become larger with higher carbon numbers. The predicted densities of mono-, di- and triglycerides formed with the same fatty acid fragment decline in turn at the same temperature. The difference between the diglyceride and the triglyceride densities has no obvious change with the increment of carbon number of the constituent fatty acid. However, the gap between the monoglyceride and the triglyceride densities decreases for the components with the longer fatty acid fragments, contrary to vapor pressure and heat capacity.

Comparisons of Estimates of Triglyceride Mixture Properties
Vapor Pressure of Soybean Oil The triglyceride composition of soybean oil is shown in Table 9. See Ndiaye, P. M., Tavares, F. W., Dalmolin, I., Dariva, C., Oliveira, D., and Oliveira, J. V., "Vapor Pressure Data of Soybean Oil, Castor Oil, and Their Fatty Acid Ethyl Ester Derivatives," *Journal of Chemical and Engineering Data*, 50, 330-333 (2005).

TABLE 9

Triglyceride Composition of Soybean Oil

| Fatty Acid Chain | Triglyceride | Mole Fraction in Soybean Oil |
|---|---|---|
| C16:0 | PPP | 0.0379 |
| C18:0 | SSS | 0.1114 |
| C18:1 | OOO | 0.2346 |
| C18:2 | LiLiLi | 0.5439 |
| C18:3 | LnLnLn | 0.0692 |

Figure 24:
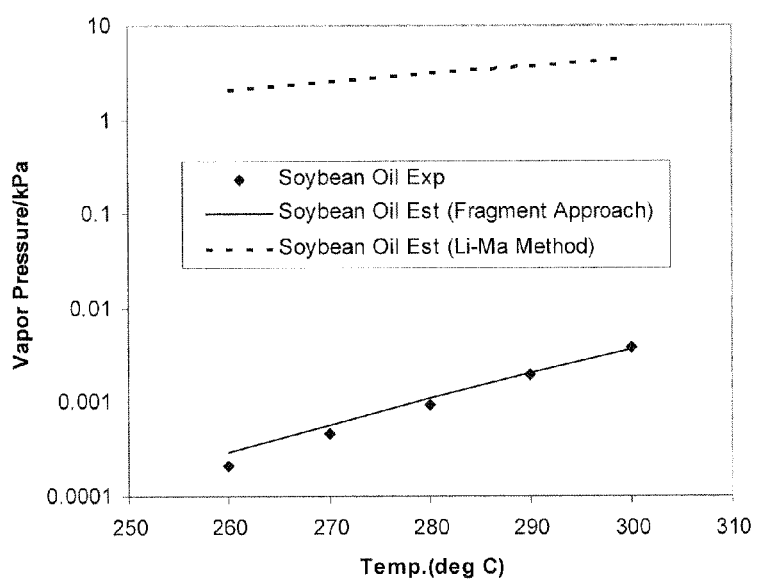
FIG. 24 is a graph of predicted vapor pressure of soybean oil, experimental data from Perry et al.

To predict the vapor pressure of triglyceride mixtures, applicants estimate the vapor pressure for each triglyceride component in the oil using the vapor pressure model and the constituent fragment-based method. The mole fraction average mixing rule described above (Dalton's law) is then used to calculate the vapor pressure of the oil, using Eq. 8. The ideal solution assumption is reasonable given that the triglyceride components are similar in structure and size. FIG. 24 shows the vapor pressure of soybean oil as a function of temperature. Also shown are the predicted results from the Li-Ma group contribution method. As shown in FIG. 24, the vapor pressure estimates from the constituent fragment-based method are in good agreement with experimental data, while the results from the Li-Ma group contribution method are orders of magnitude too large.

Enthalpy of Vaporization of Soybean Oil

The heat of vaporization for triglyceride mixtures can be estimated based on heat of vaporization for each triglyceride in the oil and the following mole fraction average mixing rule:

$$\Delta H_{\theta,oil}^{vap} = \sum_{i=1}^{n} x_i \Delta H_{\theta,i}^{vap} \quad (19)$$

where
$\Delta H_{\theta,oil}^{vap}$: Heat of vaporization of the oil, (J/kmol)
$x_i$: Mole fraction of triglyceride component i
n: Number of triglyceride components of the oil
$\Delta H_{\theta,i}^{vap}$: Heat of vaporization of triglyceride component i, (J/kmol).

The heat of vaporization of soybean oil can be estimated based on the triglyceride composition listed in Table 9. The standard (298.15 K) heat of vaporization of soybean oil estimated with the constituent fragment-based method at 1.610E+8 J/kmol is in good agreement with the experimental value of 1.847E+8 J/kmol derived from Perry. See Perry, E. S., Weber, W. H., Daubert, B. F., "Vapor Pressure of Phlegmatic Liquids I. Simple and Mixed Triglycerides," *Journal of American Chemical Society*, 71, 3720-3726 (1949).

Liquid Heat Capacity of RBDPO and Cocoa Butter

Triglyceride compositions and liquid heat capacities of refined, bleached, deodorized palm oil (RBDPO) and cocoa butter are available, and listed in Table 10. See Morad, N. A., Kamal, A. A. M., Panau, F., Yew, T. W., "Liquid Specific Heat Capacity Estimation for Fatty Acids, Triacylglycerols, and Vegetable Oils Based on Their Fatty Acid Composition," *Journal of the American Oil Chemists' Society*, 77, 1001-1005 (2000).

TABLE 10

Triglyceride Composition of RBDPO and Cocoa Butter

| | | Mass Fraction | |
|---|---|---|---|
| Fatty Acid Chain | Triglyceride | Cocoa butter | Palm oil (RBDPO) |
| C16:0 | PPP | 0.2594 | 0.4395 |
| C18:1 | OOO | 0.3308 | 0.4386 |
| C14:0 | MMM | 0 | 0.0011 |
| C18:2 | LiLiLi | 0.0231 | 0.0944 |
| C18:0 | SSS | 0.3825 | 0.0265 |
| C20:0 | AAA | 0.0042 | 0 |

The heat capacities of the oils can be estimated using Eq. 20:

$$C_{P,oil}^{l} = \sum_{i=1}^{n} w_i C_{P,i}^{l} \quad (20)$$

where
$C_{P,oil}^{l}$: Liquid heat capacity of the oil, (J/kmol-K)
$w_i$: Mass fraction of triglyceride component i
n: Number of triglyceride components in the oil
$C_{P,i}^{l}$: Liquid heat capacity of triglyceride component i, (J/kmol-K).

Figure 25:
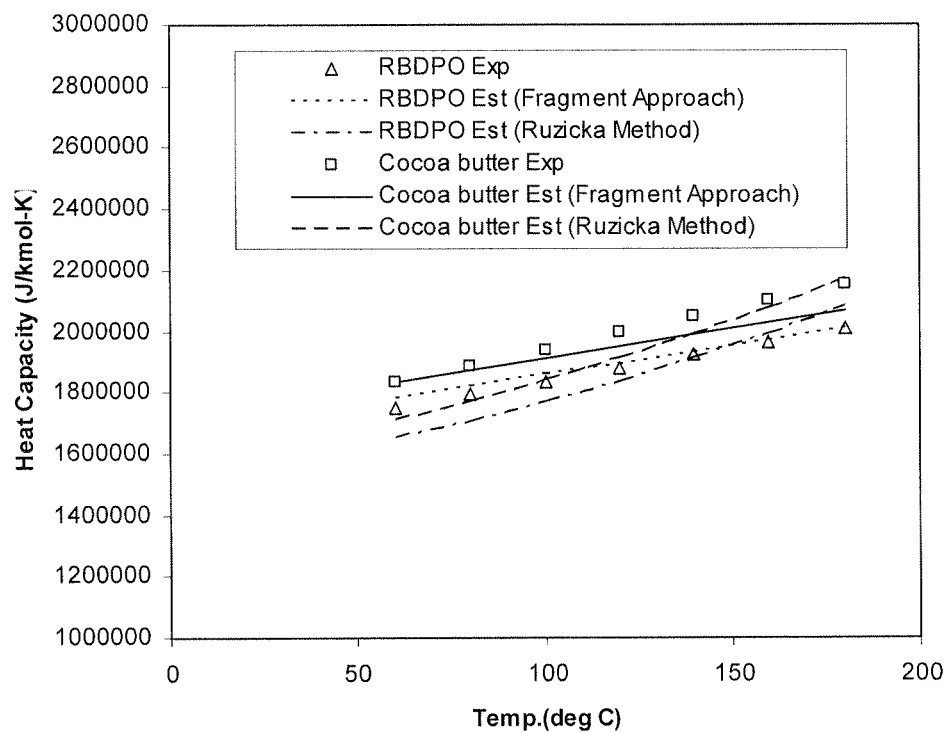
FIG. 25 is a graph of predicted liquid heat capacity of oils, experimental data from Morad et al.

FIG. 25 shows the predicted heat capacities of RBDPO and cocoa butter as a function of temperature using the constituent fragment-based method and the Ruzicka group contribution method. The results of the constituent fragment-based method are in good agreement with the experimental data.

Liquid Densities of Three Vegetable Oils

The triglyceride compositions of three vegetable oils, Brazil nut, Buriti, and grape seed, are shown in Table 11. Densities of the three vegetable oils are available. See Ceriani, R., Paiva, F. R., Goncalves, C. B., Batista, E. A. C., Meirelles, A. J. A., "Densities and Viscosities of Vegetable Oils of Nutritional Value," *Journal of Chemical and Engineering Data*, 53, 1846-1853 (2008).

TABLE 11

Triglyceride Composition of Oils

| | Mass Fraction | | |
|---|---|---|---|
| Triglyceride | Brazil nut | Buriti | Grape seed |
| OOO | 0.1379 | 0.4573 | 0.0373 |
| LiLiLi | 0.0386 | 0 | 0.3298 |
| POS | 0.0408 | 0.0094 | 0 |
| SOS | 0.0139 | 0 | 0 |
| POO | 0.1185 | 0.3521 | 0.0177 |
| SOO | 0.0615 | 0.0258 | 0.0064 |
| MSO | 0.0341 | 0.0677 | 0 |
| PLiP | 0.0334 | 0.0070 | 0.0095 |
| PLiO | 0.1508 | 0.0204 | 0.0650 |
| PLiLi | 0.0719 | 0.0118 | 0.1114 |
| OOLi | 0.1748 | 0.0253 | 0.1336 |
| OLiLi | 0.1238 | 0.0233 | 0.2894 |

The mass fraction averaging rule is used to estimate the densities of these three oils:

$$\frac{1}{\rho_{oil}} = \sum_{i=1}^{n} w_i \frac{1}{\rho_i} \quad (21)$$

where
$\rho_{oil}$: Liquid density of the oil, (g/cm$^3$)
$w_i$: Mass fraction of triglyceride component i
n: Number of triglyceride components in the oil
$\rho_i$: Liquid density of triglyceride component i, (g/cm$^3$).

Figure 26:
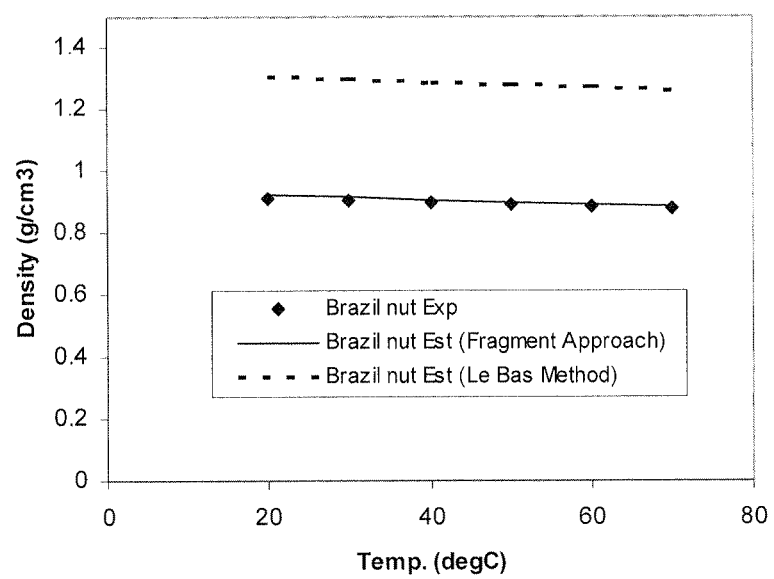
FIG. 26 is a graph of predicted density of Brazil nut oil, experimental data from Ceriani et al.
Figure 27:
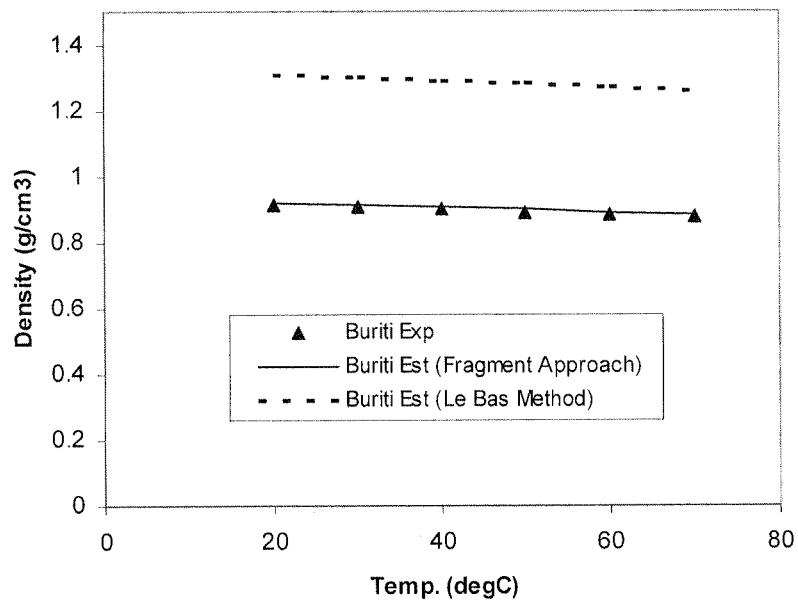
FIG. 27 is a graph of predicted density of Buriti oil, experimental data from Ceriani et al.
Figure 28:
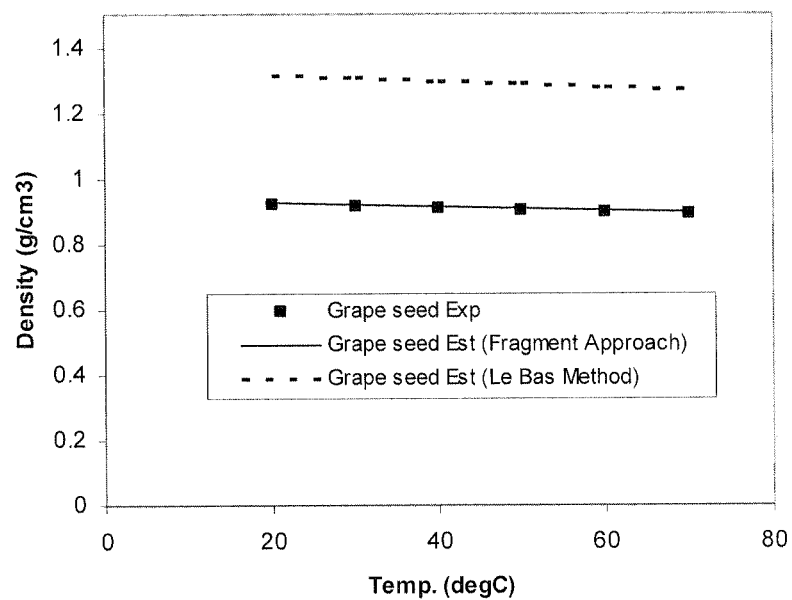
FIG. 28 is a graph of predicted density of grape seed oil, experimental data from Ceriani et al.

FIGS. 26-28 show the estimated densities of Brazil nut, Buriti, and grape seed oils, respectively, as a function of temperature, using the constituent fragment-based method. Also shown are the predicted results from the Le Bas group contribution method. The predicted densities with the fragment-based method are in good agreement with the experimental data.

Liquid Viscosities of Three Vegetable Oils

Experimental data for the viscosities of three vegetable oils, Brazil nut, Buriti and grape seed, are available. See Ceriani, R., Paiva, F. R., Goncalves, C. B., Batista, E. A. C., Meirelles, A. J. A., "Densities and Viscosities of Vegetable Oils of Nutritional Value," *Journal of Chemical and Engineering Data*, 53, 1846-1853 (2008). The viscosities were estimated based on the following weight fraction average mixing rule and the triglyceride composition shown in Table 11:

$$\ln\eta_{oil} = \sum_{i=1}^{n} w_i \ln\eta_i \quad (22)$$

where
$\eta_{oil}$: Liquid viscosity of the oil, (Pa-s)
$w_i$: Mass fraction of triglyceride component i
n: Number of triglyceride components of the oil
$\eta_i$: Liquid viscosity of triglyceride component i, (Pa-s).

Figure 29:
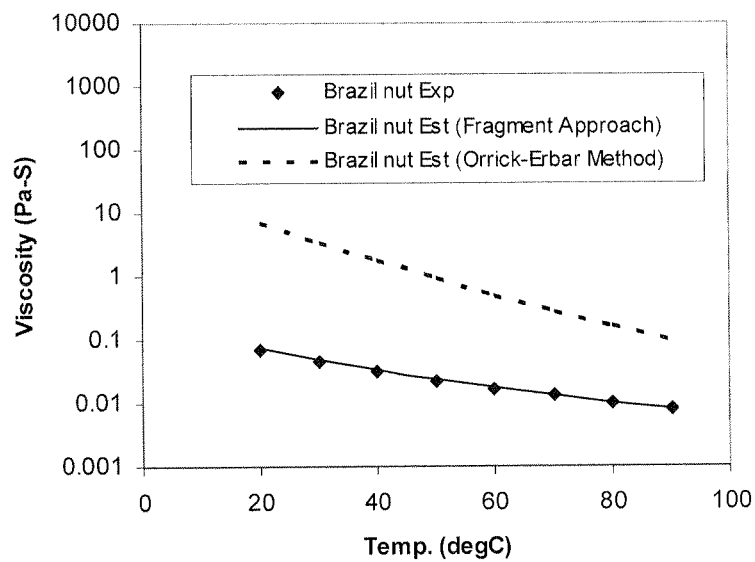
FIG. 29 is a graph of predicted liquid viscosity of Brazil nut oil, experimental data from Ceriani et al.
Figure 30:
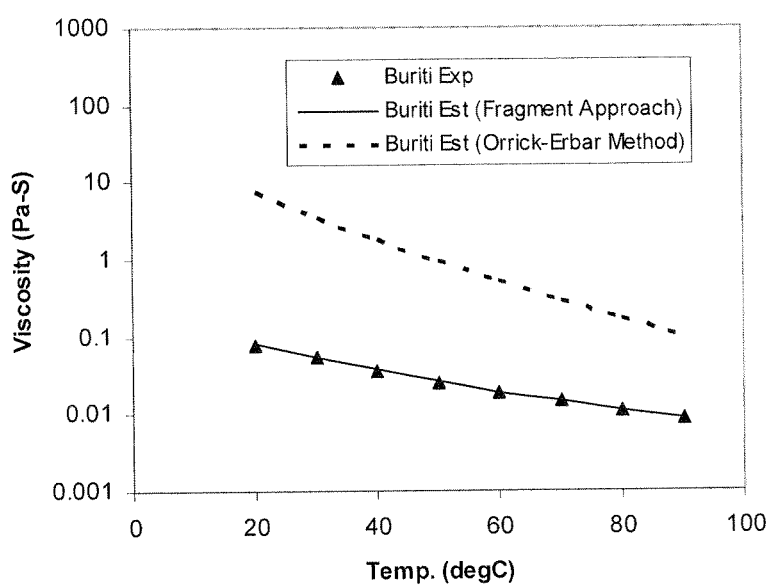
FIG. 30 is a graph of predicted liquid viscosity of Buriti oil, experimental data from Ceriani et al.
Figure 31:
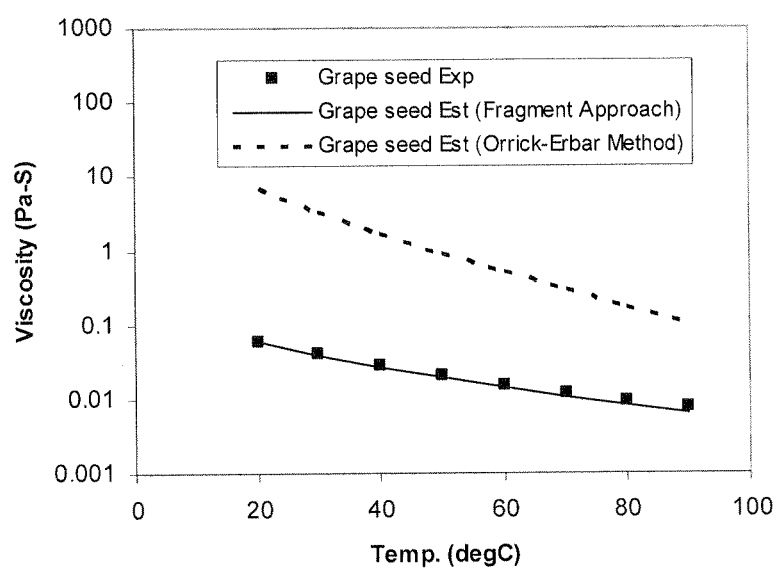
FIG. 31 is a graph of predicted liquid viscosity of grape seed oil, experimental data from Ceriani et al.

FIGS. 29-31 show the viscosity of Brazil nut, Buriti, and grape seed oils, respectively, as function of temperature. The predicted results from the Orrick-Erbar group contribution method are also graphed as the dashed lines. The liquid viscosities predicted with the constituent fragment-based method for the three oils are in good agreement with the experimental data.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-implemented method of modeling physical properties of monoglycerides, diglycerides, and triglycerides in biodiesel feedstock comprising:
   in a processor:
   (i) estimating values of a molecular physical property of constituent fatty acid fragments bound to a subject monoglyceride, diglyceride, or triglyceride molecule in biodiesel feedstock by computing physical property parameters for a constituent fatty acid fragment by regression of known values of the molecular physical property of literature monoglycerides, diglycerides, and triglycerides containing the constituent fatty acid fragments, wherein the literature monoglycerides, diglycerides, and triglycerides are different from the subject monoglyceride, diglyceride, or triglyceride molecule;
   (ii) computing a value of the molecular physical property of the subject monoglyceride, diglyceride, or triglyceride molecule by expressing the value of the molecular physical property of the subject monoglyceride, diglyceride, or triglyceride molecule as a function of the estimated values of the molecular physical property of constituent fatty acid fragments bound to the subject monoglyceride, diglyceride, or triglyceride molecule;
   (iii) repeating steps (i) and (ii) for different monoglycerides, diglycerides, or triglycerides, resulting in a plurality of computed values of the molecular physical property of different monoglycerides, diglycerides, and triglycerides; and
   (iv) using the resulting plurality, determining a value of a subject molecular physical property of a biodiesel feedstock by expressing the value of the subject molecular physical property of the biodiesel feedstock as a sum of values from the resulting plurality of the computed molecular physical property values corresponding to constituent monoglycerides, diglycerides, and triglycerides of the biodiesel feedstock, wherein the determined value of the subject molecular physical property enables modeling and blending of the biodiesel feedstock in production of biodiesel; and displaying on a computer monitor a model of the biodiesel feedstock in production of biodiesel resulting from the computed and determined value of the subject physical property of the biodiesel feedstock.

2. The method of claim 1, wherein the molecular physical property of the subject monoglyceride, diglyceride, or triglyceride molecule includes any one of vapor pressure, enthalpy of vaporization, Gibbs free energy of vaporization, liquid heat capacity, enthalpy of fusion, enthalpy of formation, liquid molar volume, viscosity, or any combination thereof.

3. The method of claim 1, wherein the biodiesel feedstock includes any of fats, oils, and combinations thereof.

4. A method as claimed in claim 1, wherein:
   the step of repeating includes for a given monoglyceride repeating steps (i) and (ii) to compute values of different physical properties of the given monoglyceride, resulting in a plurality of computed values of different physical properties of different monoglycerides;
   the step of repeating includes for a given diglyceride repeating steps (i) and (ii) to compute values of different physical properties of the given diglyceride, resulting in a plurality of computed values of different physical properties of different diglycerides; and
   the step of repeating includes for a given triglyceride repeating steps (i) and (ii) to compute values of different physical properties of the given triglyceride, resulting in a plurality of computed values of different physical properties of different triglycerides.

5. A method as claimed in claim 4, further comprising the step of storing the resulting plurality of computed monoglyceride physical property values, diglyceride property values, and triglyceride physical property values in a searchable data store.

6. A data store formed by the method of claim 5.

7. A biodiesel production modeling system comprising:
   a) a data store holding a plurality of molecular physical property values of monoglycerides, diglycerides, and triglycerides, the data store being searchable and formed by, for each of different monoglycerides, diglycerides, or triglycerides, i) estimating values of a molecular physical property of constituent fatty acid fragments bound to a subject monoglyceride, diglyceride, or triglyceride molecule by computing physical property parameters for a constituent fatty acid fragment by regression of known values of the molecular physical property of literature monoglycerides, diglycerides, and triglycerides containing the constituent fatty acid fragments, wherein the literature monoglycerides, diglycerides, and triglycerides are different from the subject monoglyceride, diglyceride, or triglyceride molecule, ii) computing the molecular physical property of the subject monoglyceride, diglyceride, or triglyceride by expressing a value of the molecular physical property of the subject monoglyceride, diglyceride, or triglyceride as a function of the estimated values of the molecular physical property of constituent fatty acid fragments bound to the subject monoglyceride, diglyceride, or triglyceride, and iii) storing in the data store the resulting value of the computed physical property of the subject monoglyceride, diglyceride, or triglyceride molecule; and
   b) a modeler coupled to receive from the data store molecular physical property values of monoglycerides, diglycerides, and triglycerides, the modeler using the stored computed physical property values of monoglycerides, diglycerides, and triglycerides to determine a value of the molecular physical property of a biodiesel feedstock and therefrom produce a model of the biodiesel feedstock in production of biodiesel, the modeler expressing the value of the molecular physical property of the biodiesel feedstock as a sum of stored computed molecular physical property values of monoglycerides, diglycerides, and triglycerides corresponding to constituent monoglycerides, diglycerides, and triglycerides of the biodiesel feedstock.

8. The system of claim 7, wherein the molecular physical property of the subject monoglyceride, diglyceride, or triglyceride molecule includes any one of vapor pressure, enthalpy of vaporization, Gibbs free energy of vaporization, liquid heat capacity, enthalpy of fusion, enthalpy of formation, liquid molar volume, viscosity, or any combination thereof.

9. The system of claim 7, wherein the biodiesel feedstock includes any of fats, oils, and combinations thereof.

* * * * *